(12) United States Patent
Kim et al.

(10) Patent No.: US 10,858,321 B2
(45) Date of Patent: Dec. 8, 2020

(54) COMPOSITION FOR INDUCING CELL REPROGRAMMING

(71) Applicant: GWANGJU INSTITUTE OF SCIENCE AND TECHNOLOGY, Gwangju (KR)

(72) Inventors: Yong Chul Kim, Gwangju (KR); Darren R. Williams, Gwangju (KR); Da Woon Jung, Gwangju (KR); Jung Eun Lee, Seoul (KR); Shin Ae Seo, Damyang-gun (KR); Ji Yeon Park, Yeosu-si (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 602 days.

(21) Appl. No.: 15/323,342

(22) PCT Filed: Jun. 30, 2015

(86) PCT No.: PCT/KR2015/006718
§ 371 (c)(1),
(2) Date: Dec. 30, 2016

(87) PCT Pub. No.: WO2016/003169
PCT Pub. Date: Jan. 7, 2016

(65) Prior Publication Data
US 2017/0158642 A1 Jun. 8, 2017

(30) Foreign Application Priority Data
Jul. 1, 2014 (KR) .................. 10-2014-0081889

(51) Int. Cl.
C07D 231/56 (2006.01)
A61K 31/416 (2006.01)
A61K 31/415 (2006.01)
C07D 401/12 (2006.01)
C12N 5/077 (2010.01)

(52) U.S. Cl.
CPC .......... *C07D 231/56* (2013.01); *A61K 31/415* (2013.01); *A61K 31/416* (2013.01); *C07D 401/12* (2013.01); *C12N 5/0654* (2013.01); *C12N 2506/1323* (2013.01)

(58) Field of Classification Search
None
See application file for complete search history.

(56) References Cited

U.S. PATENT DOCUMENTS

| 5,244,907 | A | * | 9/1993 | Munson, Jr. | ......... C07D 471/08 514/299 |
| 6,462,039 | B1 | * | 10/2002 | Hillebrand | ............. A01N 43/88 514/229.2 |
| 8,288,425 | B2 | | 10/2012 | Edwards et al. | |
| 8,372,850 | B2 | | 2/2013 | Jimenez et al. | |
| 2004/0014802 | A1 | | 1/2004 | Dutruc-Rosset et al. | |
| 2005/0234095 | A1 | * | 10/2005 | Xie | ...................... C07D 453/02 514/305 |
| 2006/0004000 | A1 | | 1/2006 | D'Orchymont et al. | |
| 2006/0079564 | A1 | * | 4/2006 | Jansen | ................. C07D 403/04 514/394 |
| 2007/0232620 | A1 | | 10/2007 | Dorsh et al. | |
| 2009/0118278 | A1 | | 5/2009 | Forster et al. | |
| 2010/0292207 | A1 | * | 11/2010 | Lombardi Borgia | ....................... C07D 231/56 514/210.21 |
| 2011/0034441 | A1 | * | 2/2011 | Hood | ................... A61K 31/416 514/218 |
| 2012/0053345 | A1 | * | 3/2012 | Ericson | ................ C07D 403/12 544/280 |
| 2012/0108619 | A1 | * | 5/2012 | Griffith | ................ C07D 519/00 514/278 |
| 2013/0281399 | A1 | * | 10/2013 | McLure | ............... C07D 239/91 514/43 |
| 2015/0065482 | A1 | * | 3/2015 | Blaquiere | ............ C07D 401/14 514/210.18 |

FOREIGN PATENT DOCUMENTS

JP 09022097 A * 1/1997
KR 10-2013-0085752 A 7/2013
(Continued)

OTHER PUBLICATIONS

Swain et al. J. Med. Chem. (1991) 34: 140-151 (Year: 1991).*
Selvaraj et al. Trends in Biotechnology (2010) 24(4): 214-223 (Year: 2010).*
Holmberg et al. Nature Reviews (2012) 13: 429-439 (Year: 2012).*
Land et al. Tetrahedron (1970) 26(24): 5793-5805 (Year: 1970).*
Chemical Abstract; STN express; Total 115 pages.
Gregory R. Ott et al.,"Synthetic Studies toward 3-(Acylamino)-1H-indazoles and Development of a One-Pot, Microwave-Assisted, Oxadiazole Condensation/Boulton-Katritzky Rearrangement", Synlett, 2011, pp. 3018-3022, No. 20, XP002772190, Georg Thieme Verlag Stuttgart, New York.
(Continued)

*Primary Examiner* — Susan M Hanley
(74) *Attorney, Agent, or Firm* — Hauptman Ham, LLP

(57) ABSTRACT

The present invention relates to a composition for inducing cell reprogramming. The indazole derivative compound contained in the composition of the present invention shows an improved biological profile and at the same time can perform efficient cell reprogramming. In addition, unlike conventional compounds (e.g. riversine or BIO) for inducing low-molecular cell reprogramming, the indazole derivative compound of the present invention does not show cytotoxicity and thus is expected to have high growth in the market of cell therapy products when clinically applied. Conventional indazole derivative compounds have never known as a use for cell reprogramming. Compared with conventional indazole derivative compounds, the compound of the present invention has a great cell reprogramming ability while having no or little cytotoxicity.

16 Claims, 4 Drawing Sheets

(56) References Cited

FOREIGN PATENT DOCUMENTS

WO  2007/117465 A2  10/2007
WO  2016/026549 A1  2/2016

OTHER PUBLICATIONS

Kwartler Charles E. et al.,"The Preparation of Sulfanilamidoindazoles", Journal of the American Chemical Society, 1943, pp. 1804-1806, vol. 65, No. 10, XP002224525, American Chemical Soeciety, US.
Jakob Meisenheimer et al.,"Uber die isomeren Acyl-indazole von K. v. Auwers.", Chemische Berichte, 1924, pp. 1715-1723, XP055391614, Chemical Institution of Tubingen University.
Data Base WPI, Week 201382, AN 2013-M53463, XP002772191,Thomson Scientific, London, GB.
Extended European Search Report dated Jul. 28, 2017 from European Patent Office in connection with the counterpart European Patent Application No. 15815352.8.

* cited by examiner

COMPOSITION FOR INDUCING CELL REPROGRAMMING

TECHNICAL FIELD

Cross Reference to Related Application

This application claims priority to Korean Patent Application No. 10-2014-0081889, filed in the Korean Intellectual Property Office, on Jul. 1, 2014. Further, this application is the National Phase application of International Application No. PCT/KR2015/006718, filed Jun. 30, 2015, which designates the United States and was published in Korean. Both of the priority documents are hereby incorporated by reference in their entireties.

The present invention relates to a composition for inducing cell reprogramming.

Background Art

As an aging society has been growing, many people have suffered from degenerative diseases, and the number thereof has continued to increase. The most ideal method for treatment of a number of incurable degenerative diseases, including Parkinson's disease and Lou Gehrig's disease, is to transplant either pluripotent stem cells, derived from the patient, or functional cells that differentiated therefrom, into an affected part. In recent years, for radical treatment of incurable degenerative diseases, a competition for development of technologies among countries in the world to lead the development of cell therapeutic agents and new arugs based on cell reprogramming technology has been keenly contested.

Reprogramming technology is a relatively easy method that causes little or no physical damage and discomfort to patients. This technology makes it possible to obtain self-somatic cells and to produce induced pluripotent stem cells having characteristics similar to those of human embryonic stem cells therefrom. Thus, it dramatically evolved a strategy for generating self pluripotent stem cells from patient's somatic cells. For example, virus recombined with a specific gene may be used to induce undifferentiated stem cells, and several researchers reported a method in which the virus is transfected into cells to insert the gene into the genome of the cells and the protein of interest is expressed in the cells. Meanwhile, reprogrammed cells produced by this method were found to have cell characteristics and differentiation potential, which are almost similar to those of embryonic stem cells, but these cells have a problem in that they contain a large amount of a genetic material on the genome of the cells, because the gene is delivered into the cells by the viral vector. In addition, in vivo experiments indicated that induced pluripotent stem cells had side effects such as formation of cancer. This suggests that the actual clinical application of induced pluripotent stem cells can still be risky.

As described above, induced pluripotent stem cells have a problem in that an oncogene is used in a reprogramming process. Due to this problem, in recent years, there have been active studies on direct reprogramming to allow somatic cells to differentiate directly into a required cell lineage in patients, unlike conventional reprogramming methods.

Meanwhile, among conventional compounds, compounds (e.g., Reversine, Aurora kinase inhibitor) which can be used for cell reprogramming are not suitable as a cell reprogramming composition due to their cytotoxicity.

The present inventors have made extensive efforts to overcome the above-described problems, and as a result, have synthesized compounds which are not toxic to cells and which allow direct reprogramming of differentiated cells into cells having other characteristics, and have found that the use of these compounds enables safe, efficient cell reprogramming.

Throughout the specification, a number of publications and patent documents are referred to and cited. The disclosure of the cited publications and patent documents is incorporated herein by reference in its entirety to more clearly describe the state of the related art and the present invention.

DISCLOSURE

Technical Problem

The present inventors have made extensive efforts to develop compositions capable of inducing cell reprogramming while showing improved biological profiles compared to conventional indazole derivative compounds. As a result, the present inventor have designed and synthesized novel indazole derivative compounds having the ability to induce cell reprogramming, and have found that these compounds have excellent cell reprogramming ability without showing cytotoxicity, unlike conventional indazole derivatives (for example, kinase inhibitors), thereby completing the present invention.

Therefore, it is an object of the present invention to provide a composition for inducing cell reprogramming.

Another object of the present invention is to provide novel indazole derivatives.

Other objects and advantages of the present invention will be more apparent from the following detailed description, the accompanying drawings and the appended claims.

Technical Solution

In accordance with one aspect, the present invention provides a composition for inducing cell reprogramming, comprising a compound represented by the following formula A:

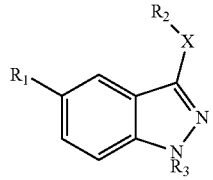

Formula A wherein $R_1$ is hydrogen, nitro, nitroxy or Y-carbonyl, wherein Y is hydrogen, hydroxy, halo, $C_{1-30}$ alkoxy, $C_{2-30}$ heterocycloalkyl containing nitrogen, oxygen or sulfur as a heteroatom, $C_{2-20}$ heterocycloalkenyl containing nitrogen, oxygen or sulfur as a heteroatom, $C_{6-30}$ aryl, $C_{1-30}$ alkyl, or $C_{2-30}$ alkenyl; $R_2$ is hydrogen, hydroxy, halo, $C_{1-30}$ aryl, $C_{1-30}$ alkoxy, $C_{1-30}$ alkyl, or $C_{2-30}$ alkenyl; $R_3$ is hydrogen, hydroxy, halo, $C_{1-30}$ aryl, $C_{1-30}$ alkoxy, $C_{1-30}$ alkyl, or $C_{2-30}$ alkenyl; and X is amine, amido, sulfonamido, carbonyl, oxime, or imidamido.

According to another aspect, the present invention provides a method for producing reprogrammed cells from differentiated cells, the method comprising the steps of: (a) bring a cell reprogramming composition into contact with the differentiated cells; (b) culturing the cells of step (a).

The present inventors have made extensive efforts to develop compositions capable of inducing cell reprogramming while showing improved biological profiles compared to conventional indazole derivative compounds. As a result, the present inventor have designed and synthesized novel indazole derivative compounds having the ability to induce cell reprogramming, and have found that these compounds have excellent cell reprogramming ability without showing cytotoxicity, unlike conventional indazole derivatives (for example, kinase inhibitors).

The compound represented by formula A according to the present invention is a compound that can reprogram differentiated cells into cells having new characteristics, and is chemically synthesized using indazole as a nucleus. Conventional indazole derivative compounds have not been known to be used for cell reprogramming, and the compound of the present invention has an excellent ability to reprogram cells while having little or no cytotoxicity, compared to conventional indazole derivative compounds. A conventional direct reprogramming method is a method of introducing a gene using virus, and has shortcomings in that the method is difficult to apply directly to patient, the efficiency of the process of inducing cell reprogramming is low, and immunological problems arise. Direct cell reprogramming using the low-molecular compound of the present invention is very excellent in terms of safety, cost-effectiveness and efficiency, because cell reprogramming is induced only by treatment with the low-molecular compound instead of introducing a gene by a viral vector.

The composition of the present invention is very effective for inducing reprogrammed cells from differentiated cells. According to the present invention, the composition of the present invention can induce cell lines of various lineages, such as reprogrammed osteogenic lineage cells or adipogenic lineage cells, from mammalian differentiated cells. According to one embodiment of the present invention, the composition of the present invention induces differentiation from myoblasts into osteoblasts or adipocytes.

The term "differentiated cells" is not specifically limited, and includes, for example, somatic cells or somatic stem cells. The term "somatic cells" refers to adult cells having a limited ability to differentiate and self-renew. The somatic cells may be cells that form human skin, hair, adipose or bone.

The differentiated cells may be cells from a variety of mammals, including humans, monkeys, pigs, horses, cattle, sheep, dogs, cats, mice and rabbits. Preferably, the differentiated cells may be human cells.

As used herein, the term "reprogramming" refers to a process by which cells existing in different conditions, such as cells having no differentiation potential or cells having a certain differentiation potential, can be finally restored or converted into a new type of cells or a new type of status having differentiation potential. According to the present invention, differentiated cells may be reprogrammed into cells having characteristics that are 0-100% different from those of the differentiated cells, as a result of contact with the composition of the present invention.

As used herein, the term "nitro" used to define the indazole derivatives of formula A refers to halogen group elements, and includes, for example, fluoro, chloro, bromo and iodo.

The term "nitroxy" refers to an —O—N=O functional group.

The term "carbonyl" refers to a —(C=O)— functional group.

The term "hydroxy" refers to an —OH— functional group.

The term "halo" refers to halogen group elements, and includes, for example, fluoro, chloro, bromo and iodo.

The term "alkyl" refers to a straight or branched-chain, unsubstituted or substituted, saturated hydrocarbon group, and includes, for example, methyl, ethyl, propyl, isobutyl, pentyl, hexyl, heptyl, octyl, nonyl, decyl, undecyl, tridecyl, pentadecyl and heptadecyl. "$C_{1-30}$ alkyl" refers to an alkyl group having a alkyl unit containing 1-30 carbon atoms, and when $C_{1-30}$ alkyl is substituted, the carbon number of the substituent is not included in the carbon number of the $C_{1-30}$ alkyl.

According to the present invention, the $C_{1-30}$ alkyl at the Y position in formula is $C_{1-15}$ alkyl, and the $C_{1-30}$ alkyl at the $R_2$ position in formula A is preferably $C_{1-15}$ alkyl.

The term "alkenyl" refers to a straight or branched-chain unsubstituted or substituted, unsaturated hydrocarbon group having the indicated number of carbon atoms, and includes, for example, ethenyl, vinyl, propenyl, allyl, isopropenyl, butenyl, isobutenyl, t-butenyl, n-pentenyl, and n-hexenyl. "$C_{2-20}$ alkenyl" refers to an alkenyl group having an alkenyl unit containing 2-30 carbon atoms, and when $C_{2-20}$ alkenyl is substituted, the carbon number of the substituent is not included in the carbon atom of the $C_{2-20}$ alkenyl. According to the present invention, the $C_{2-20}$ alkenyl at the Y position in formula A is $C_{2-15}$ alkenyl, and the $C_{2-20}$ alkenyl at the $R_2$ position in formula A is $C_{2-15}$ alkenyl.

The term "alkoxy" refers to an alkyl or aryl group combined with one oxygen atom, and include, for example, methoxy, ethoxy, propoxy, aryloxy and the like. "$C_{1-30}$ alkoxy" means an alkyl group having an alkoxy unit containing 1 to 30 carbon atoms, and when $C_{1-30}$ alkoxy is substituted, the carbon number of the substituent is not included in the carbon number of the $C_{1-30}$ alkoxy.

The term "alkoxyalkyl" refers to an alkyl group substituted with an alkoxy group. "$C_{2-5}$ alkoxyalkyl" means an alkoxyalkyl group having an alkoxyalkyl unit containing 2 to 5 carbon atoms, and when $C_{2-5}$ alkoxyalkyl is substituted, the carbon number of the substituent is not included in the carbon atom of the $C_{2-5}$ alkoxyalkyl.

The term "alkoxycarbonyl" refers to carbonyl substituted with alkoxy. "$C_{2-5}$ alkoxycarbonyl" means an alkoxycarbonyl group having an alkoxycarbonyl unit containing 2 to 5 carbon atoms, and when $C_{2-5}$ alkoxycarbonyl is substituted, the carbon number of the substituent is not included in the carbon atom of the $C_{2-5}$ alkoxycarbonyl.

The expression "heterocycloalkyl containing nitrogen, oxygen or sulfur as a heteroatom" refers to a non-aromatic cyclic hydrocarbon group containing carbon and hydrogen atoms and at least one heteroatom (nitrogen, oxygen or sulfur). The heteroatom is preferably nitrogen or oxygen, and most preferably, nitrogen. According to the present invention, the number of the heteroatoms is 1 to 4, or 1 to 3, or 1 to 2. "$C_{2-30}$ heterocycloalkyl" refers to a heterocycloalkyl wherein the number of carbons forming the ring structure is 2-30.

Meanwhile, the heterocycloalkyl is a wholly or partially substituted or unsubstituted carbon ring. The heterocycloalkyl may be substituted with hydroxy, halo, $C_1$-$C_5$ substituted or unsubstituted straight- or branched-chain alkyl, $C_1$-$C_5$ substituted or unsubstituted straight- or branched-chain alkoxy, $C_1$-$C_5$ substituted or unsubstituted straight- or branched-chain alkenyl, $C_{2-8}$ alkoxyalkyl, $C_{2-5}$ alkoxycarbonyl, $C_{2-8}$ heterocycloalkenyl containing nitrogen as a heteroatom,

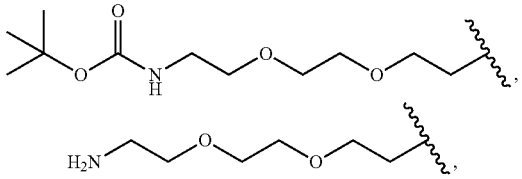

or a combination thereof.

The expression "heterocycloalkenyl containing nitrogen, oxygen or sulfur as a heteroatom" refers to a non-aromatic cyclic hydrocarbon group containing carbon and hydrogen atoms and at least one heteroatom (nitrogen, oxygen or sulfur). The heteroatom is preferably nitrogen or oxygen, and most preferably, nitrogen. According to the present invention, the number of the heteroatoms is 1 to 4, or 1 to 3, or 1 to 2. "$C_{2-30}$ heterocycloalkenyl" refers to a heterocycloalkenyl wherein the number of carbons forming the ring structure is 2-30.

The term "heterocycloalkenyl alkyl" refers to an alkyl group substituted with a heterocycloalkenyl group. "$C_{2-8}$ heterocycloalkenyl alkyl means a heterocycloalkenyl alkyl having a heterocycloalkenyl alkyl unit containing 2 to 5 carbon atoms, and when $C_{2-8}$ heterocycloalkenyl alkyl is substituted, the carbon number of the substituent is not included in the carbon number of the $C_{2-8}$ heterocycloalkenyl alkyl.

The term "aryl" refers to a wholly or partially substituted or unsubstituted monocyclic or polycyclic carbon ring. "$C_{6-30}$ aryl" refers to an aryl group having 6 to 30 carbon atoms in the ring, and when $C_{6-30}$ aryl is substituted, the carbon number of the substituent is not included in the carbon number of the $C_{6-30}$ aryl. Preferably, aryl is monoaryl or biaryl. Monoaryl preferably has 5 to 6 carbon atoms, and biaryl preferably has 9 to 10 carbon atoms. According to the present invention, the aryl is substituted or unsubstituted aryl. When monoaryl, for example, phenyl, is substituted, it may be substituted with various substituents at various position. For example, it may be substituted with halo, hydroxy, nitro, $C_1$-$C_5$ substituted or unsubstituted straight or branched-chain alkyl, $C_1$-$C_5$ substituted or unsubstituted straight or branched-chain alkenyl, $C_1$-$C_5$ substituted or unsubstituted straight or branched-chain alkoxy, $C_1$-$C_5$ substituted or unsubstituted straight or branched-chain alkyl, or a combination thereof.

Particularly preferred aryl moieties include, but are not limited to, phenyl, benzyl, naphthyl, pyrrolyl, pyrrolidinyl, pyridinyl, pyrimidinyl, purinyl, quinolinyl, isoquinolinyl, furyl, thiophenyl, thiophenyl, imidazolyl, oxazolyl, thiazolyl, pyrazolyl and thienyl.

The term "amine" refers to a functional group containing a basic nitrogen atom with a lone pair. "$C_{1-10}$ amine" refers to an amine group that has —$NH_2$ or an amine unit containing 1 to 10 carbon atoms. When $C_{1-10}$ amine is substituted, the carbon atom of the substituent is not included in the carbon atom of the $C_{1-10}$ amine. According to the present invention, the $C_{1-10}$ amine at the X position in formula A is $C_{1-5}$ amine or —$NH_2$.

The term "amide" refers to a functional group consisting of an acyl group combined with a nitrogen atom. "$C_{1-10}$ amide" refers to an amide group having an amide unit containing 1 to 10 carbon atoms. When $C_{1-10}$ amide is substituted, the carbon number of the substituent is not included in the carbon number of the $C_{1-10}$ amide.

According to the present invention, the amide is R—CO—NH—R', sulfonamide or phosphoramide.

The term "oxime" refers to a functional group comprising an imine of RR'C=N—OH.

The term "imidamide" refers to a functional group comprising N—CR=N'$H_2$.

According to the present invention, Y in formula A is hydrogen, hydroxy, halo, $C_{1-15}$ alkoxy, $C_{2-15}$ heterocycloalkyl containing nitrogen, oxygen or sulfur as a heteroatom, $C_{2-15}$ heterocycloalkenyl containing nitrogen, oxygen or sulfur as a heteroatom, $C_{6-15}$ aryl, $C_{1-15}$ alkyl, or $C_{2-15}$ alkenyl.

According to the present invention, the heterocycloalkyl in Y of formula A may be substituted with hydroxy, halo, $C_{1-5}$ alkyl, $C_{2-5}$ alkenyl, $C_{1-5}$ alkoxy, $C_{2-8}$ alkoxyalkyl, $C_{2-8}$ alkoxycarbonyl, $C_{2-8}$ heterocycloalkenyl alkyl containing nitrogen as a heteroatom,

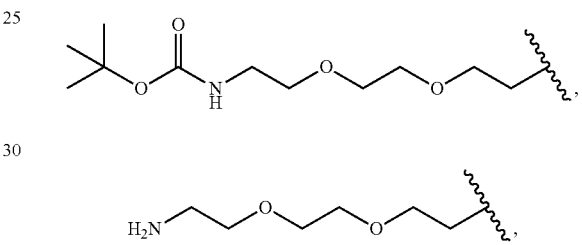

or a combination thereof.

According to one embodiment of the present invention, the heterocycloalkenyl alkyl in Y is (1H-imidazol-1-ly) alkyl.

According to the present invention, $R_2$ may be substituted with hydrogen, halo, $C_{1-15}$ aryl, $C_{1-15}$ alkoxy, or $C_{2-15}$ alkenyl, and the aryl in $R_2$ may be substituted with hydroxy, halo, $C_{1-5}$ alkoxy, $C_{1-5}$ alkyl, $C_{2-5}$ alkenyl, or a combination thereof.

Meanwhile, when X in formula A is imidamido

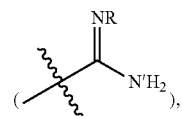

$R_2$ may be bound to C or N' of the imidamido.

The compounds of the present invention may have one or more chiral centers and/or geometric isomeric centers, and thus the present invention include all stereoisomers represented by formula A, such as optical isomers, diastereomers and geometric isomers.

According to the present invention, the composition for inducing cell reprogramming according to the present invention contains a compound represented by a formula selected from the group consisting of the following formulas 1 to 45:

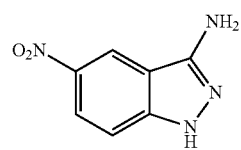
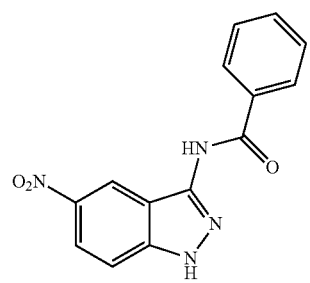
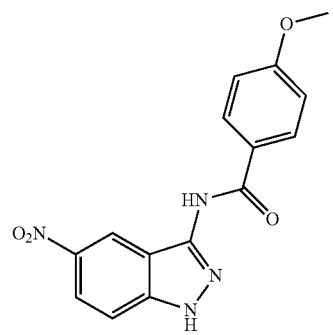
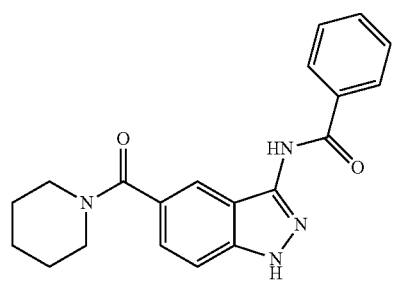
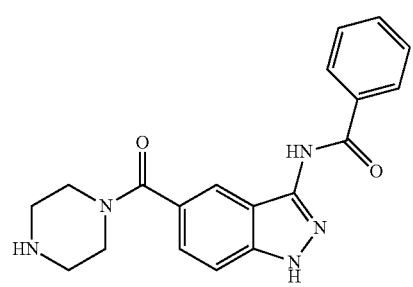
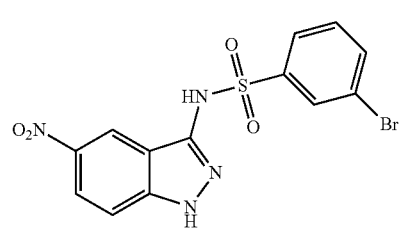
Formula 1
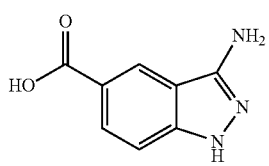
Formula 3
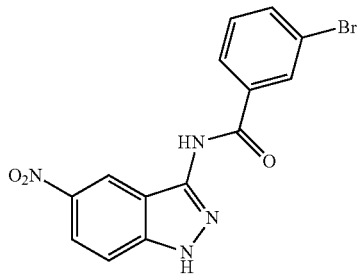
Formula 5
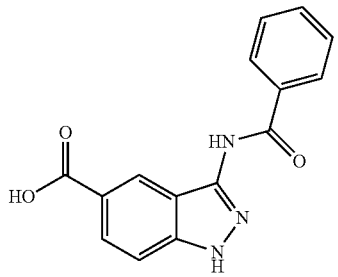
Formula 7
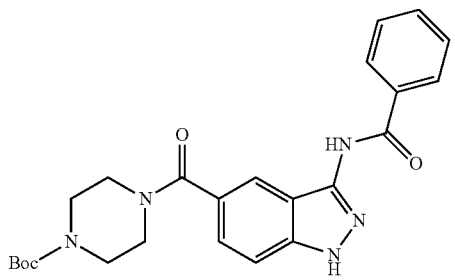
Formula 9
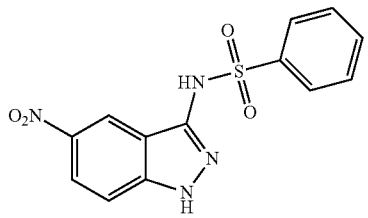
Formula 11
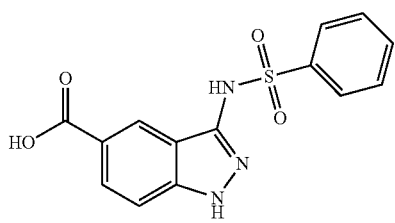
Formula 2
Formula 4
Formula 6
Formula 8
Formula 10
Formula 12

-continued
Formula 13
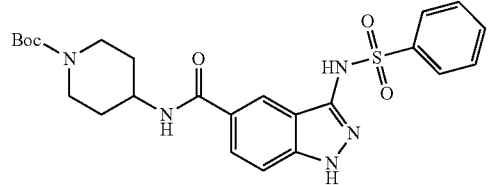
Formula 14
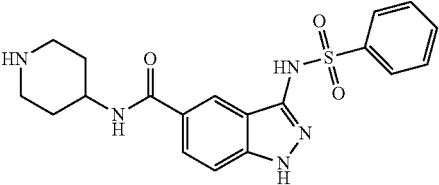
Formula 15
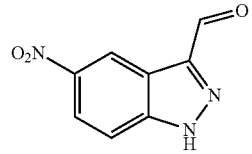
Formula 16
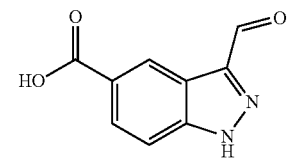
Formula 17
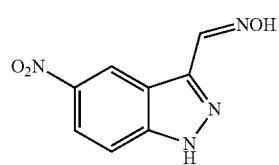
Formula 18
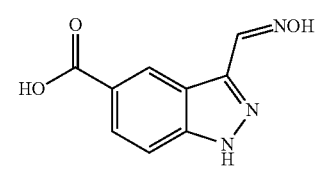
Formula 19
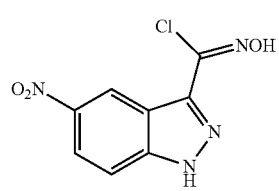
Formula 20
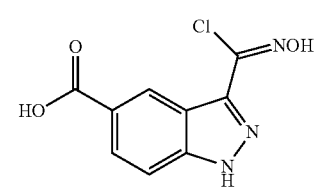
Formula 21
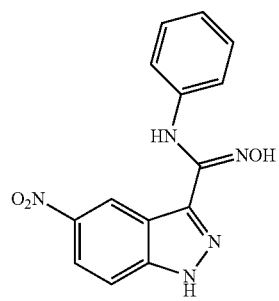
Formula 22
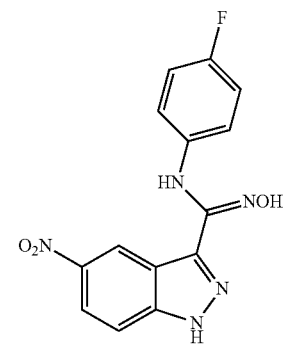
Formula 23
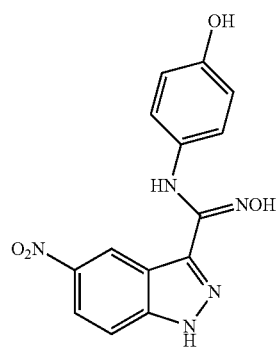
Formula 24
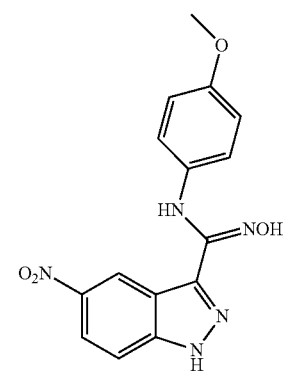

-continued
Formula 25
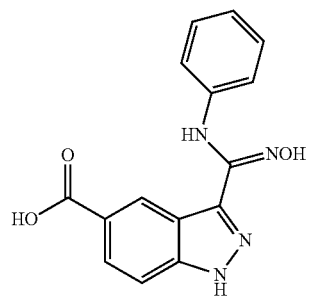
Formula 26
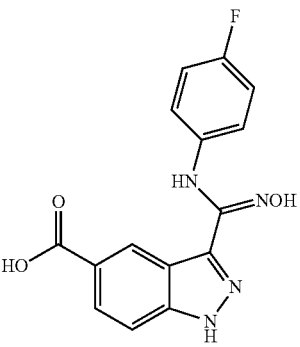
Formula 27
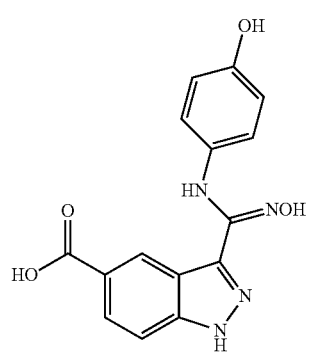
Formula 28
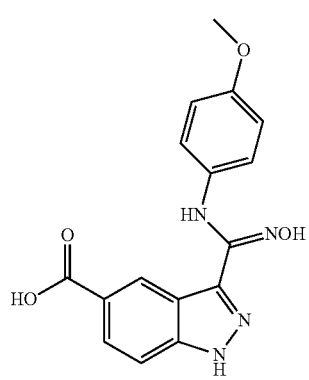
Formula 29
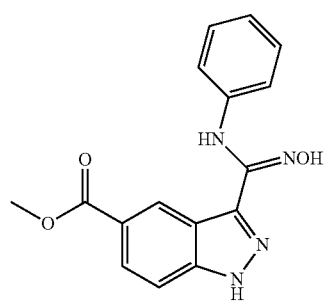
Formula 30
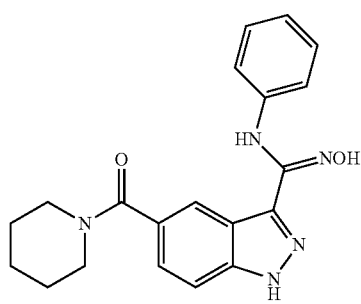
Formula 31
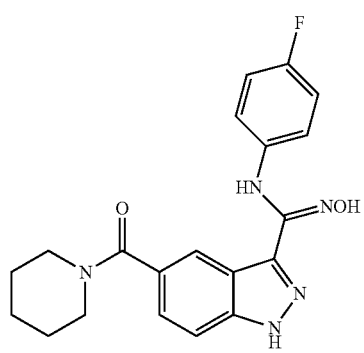
Formula 32
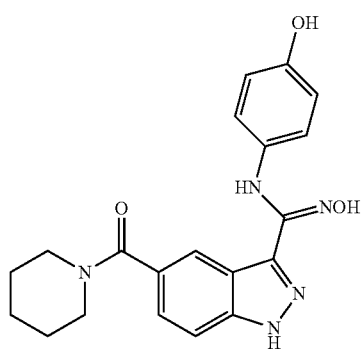

-continued
Formula 33
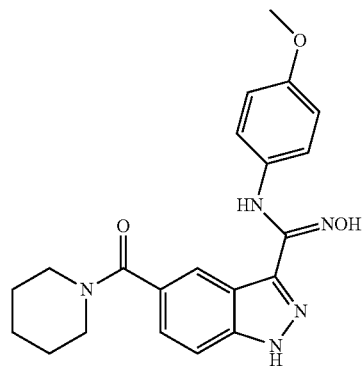
Formula 34
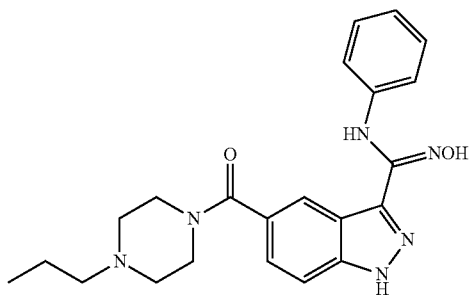
Formula 35
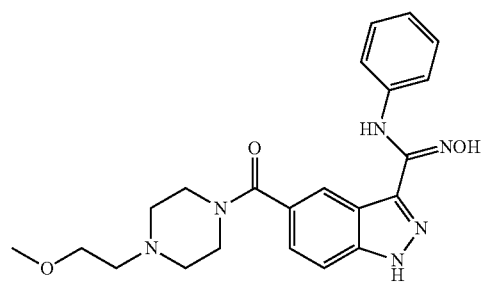
Formula 36
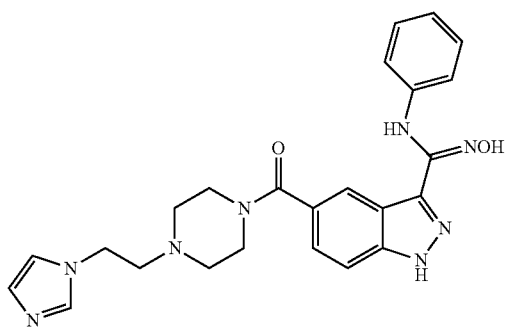
Formula 37
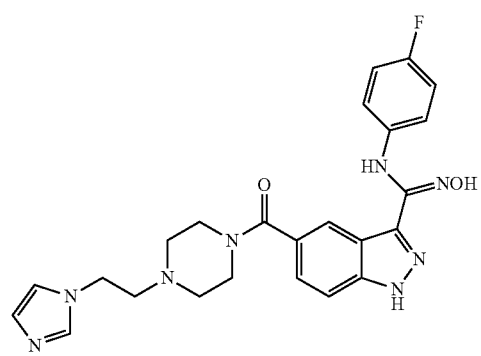
Formula 38
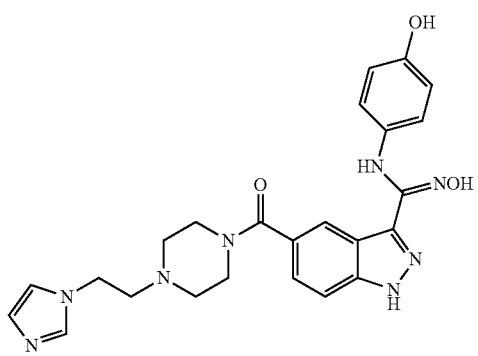
Formula 39
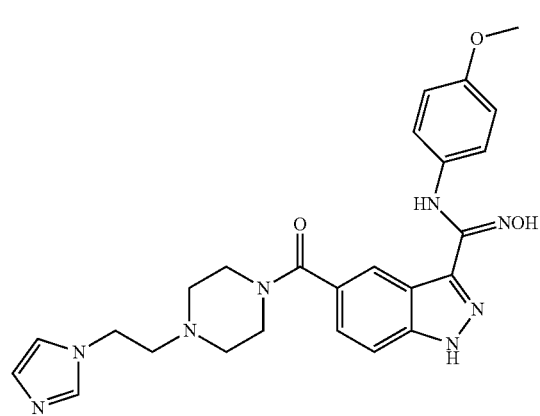

-continued

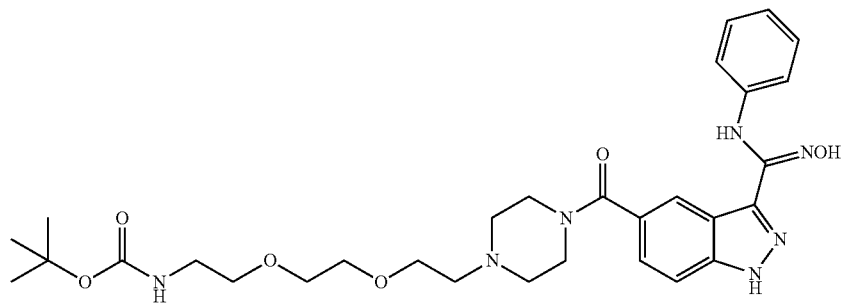

Formula 40

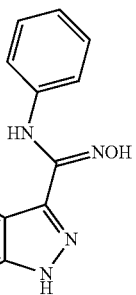

Formula 41

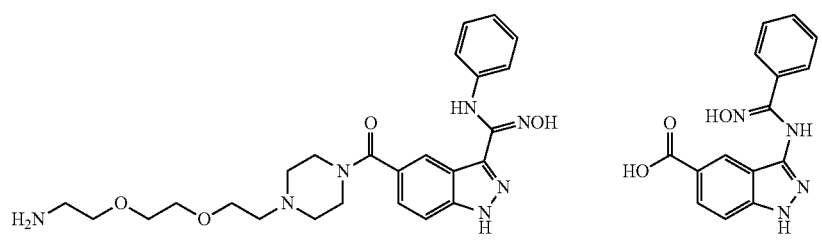

Formula 42

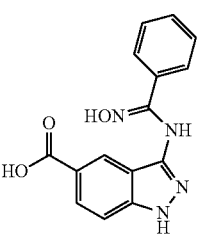

Formula 43

Formula 44

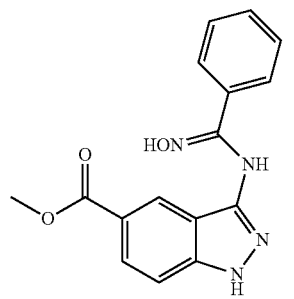

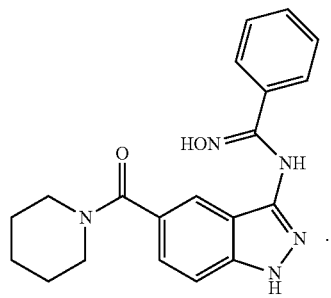

Formula 45

According to the present invention, the composition for inducing cell reprogramming according to the present invention comprises a compound represented by a formula selected from the group consisting of the following formula 1, formula 25, formula 30, formula 31, formula 33, formula 34, formula 35 and formula 45:

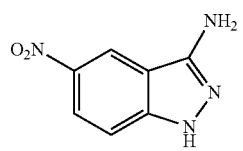

Formula 1

-continued

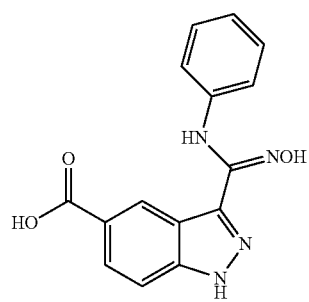

Formula 25

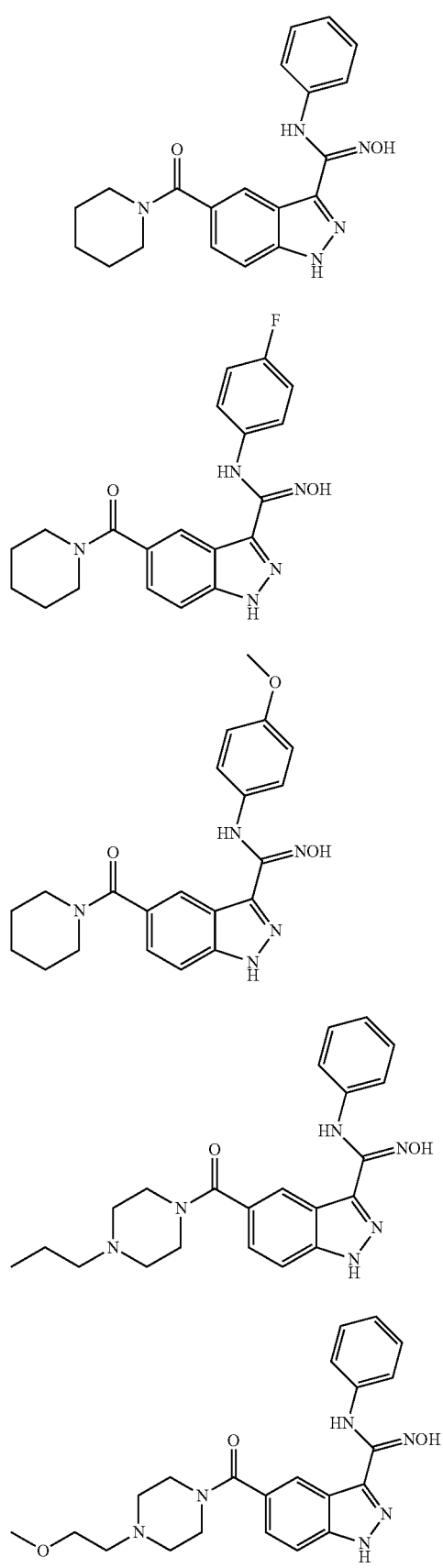

Formula 30

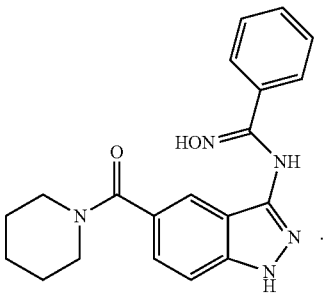

Formula 31

Formula 33

Formula 34

Formula 35

Formula 45

According to another aspect, the present invention provides an indazole derivative compound represented by the following formula A:

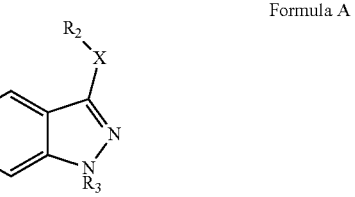

Formula A wherein $R_1$ is hydrogen, nitro, nitroxy or Y-carbonyl, wherein Y is hydrogen, hydroxy, halo, $C_{1-30}$ alkoxy, $C_{2-30}$ heterocycloalkyl containing nitrogen, oxygen or sulfur as a heteroatom, $C_{2-20}$ heterocycloalkenyl containing nitrogen, oxygen or sulfur as a heteroatom, $C_{6-30}$ aryl, $C_{1-30}$ alkyl, or $C_{2-30}$ alkenyl; $R_2$ is hydrogen, hydroxy, halo, $C_{1-30}$, aryl, $C_{1-30}$ alkoxy, $C_{1-30}$ alkyl, or $C_{2-30}$ alkenyl; $R_3$ is hydrogen, hydroxy, halo, $C_{1-30}$ aryl, $C_{1-30}$ alkoxy, $C_{1-30}$ alkyl, or $C_{2-30}$ alkenyl; and X is amine, amido, sulfonamido, carbonyl, oxime, or imidamido, provided that $R_1$ is nitro and X is amido, $R_2$ is not phenyl, and provided that when $R_1$ and $R_3$ are each hydrogen and X is N-hydroxy-imidamido and $R_2$ is phenyl, $R_2$ is not bound to the carbon atom of the imidamido (or $R_2$ is bound to the N' atom of the imidamido).

According to the present invention, Y is hydrogen, hydroxy, halo, $C_{1-15}$ alkoxy, $C_{2-15}$ heterocycloalkyl containing nitrogen, oxygen or sulfur as a heteroatom, heterocycloalkenyl containing nitrogen, oxygen or sulfur as a heteroatom, $C_{6-15}$ aryl, $C_{1-15}$ alkyl, or $C_{2-15}$ alkenyl.

According to the present invention, the heterocycloalkyl in Y of formula A may be substituted with hydroxy, halo, $C_{1-5}$ alkyl, $C_{2-5}$ alkenyl, $C_{1-5}$ alkoxy, $C_{2-8}$ alkoxyalkyl, $C_{2-8}$ alkoxycarbonyl, $C_{2-8}$ heterocycloalkenyl alkyl containing nitrogen as a heteroatom,

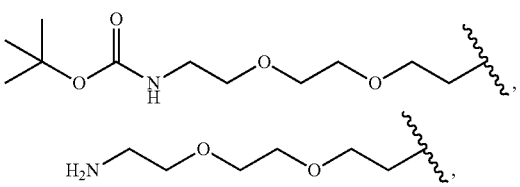

or a combination thereof. According to one embodiment of the present invention, the heterocycloalkenyl alkyl in Y is (1H-imidazol-1-ly)alkyl.

According to the present invention, R₂ in formula A may be substituted with hydrogen, halo, $C_{1-15}$ aryl, $C_{1-15}$ alkoxy, $C_{1-15}$ alkyl, or $C_{2-15}$ alkenyl, and the aryl in R₂ may be substituted with hydroxy, halo, $C_{1-5}$ alkoxy, $C_{1-5}$ alkyl, $C_{2-5}$ alkenyl, or a combination thereof.

According to one embodiment of the present invention, the heteroatom in formula A is nitrogen.

The indazole derivative compound of the present invention is represented by a formula selected from the group consisting of the following formula 1, formula 2 and formulas 4 to 45:

Formula 1

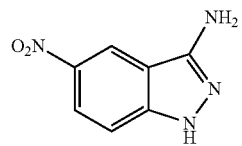

Formula 2

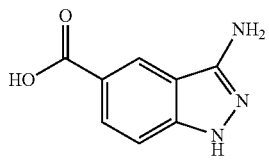

Formula 4

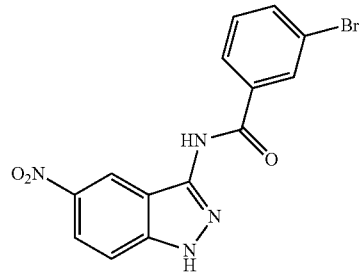

Formula 5

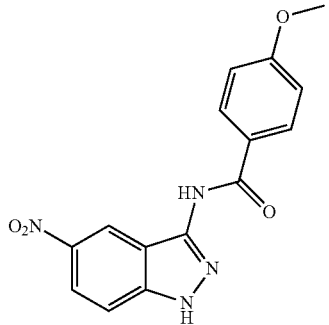

Formula 6

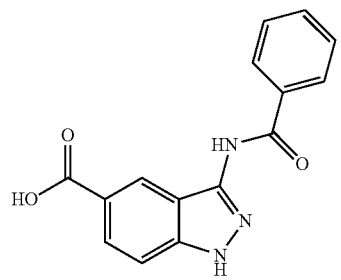

Formula 7

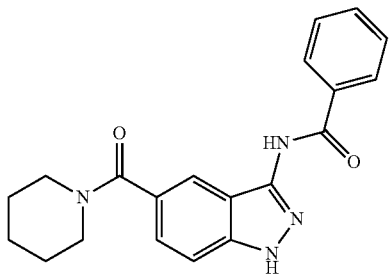

Formula 8

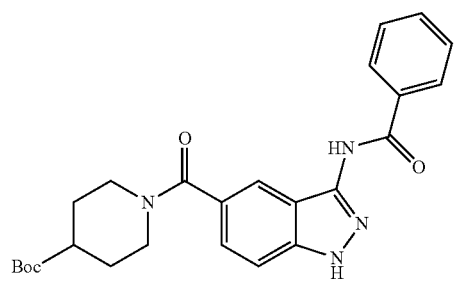

Formula 9

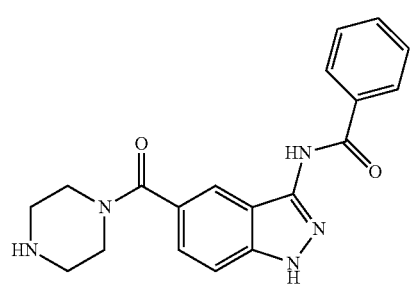

Formula 10

-continued
| Formula 11 | Formula 12 |
|---|---|
| 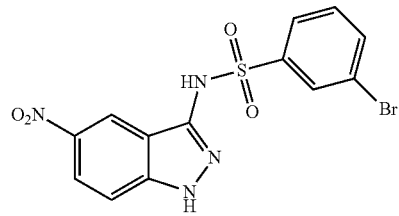 | 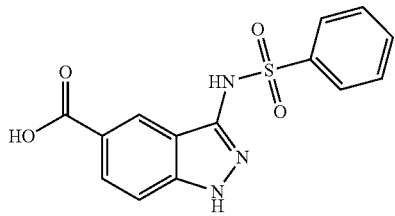 |
| Formula 13 | Formula 14 |
| 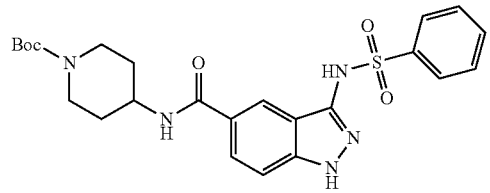 | 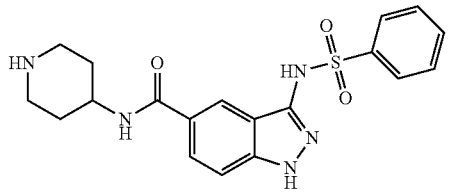 |
| Formula 15 | Formula 16 |
| 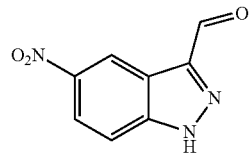 |  |
| Formula 17 | Formula 18 |
| 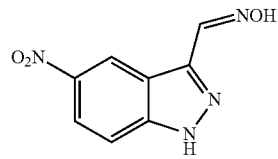 | 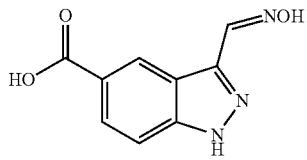 |
| Formula 19 | Formula 20 |
| 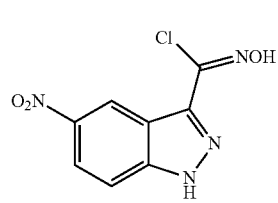 | 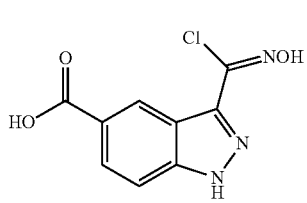 |
| Formula 21 | Formula 22 |
| 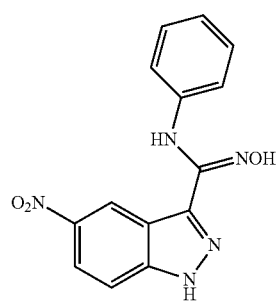 | 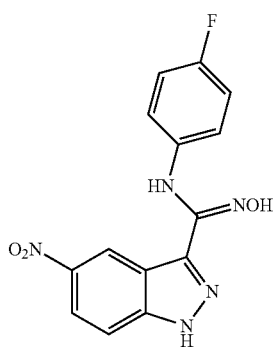 |

-continued
Formula 23
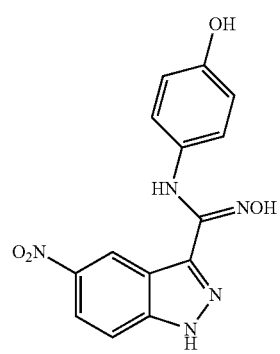
Formula 24
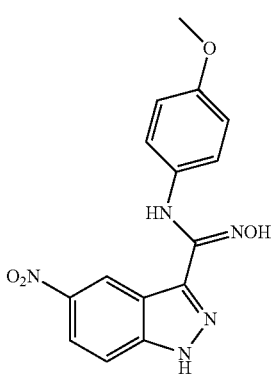
Formula 25
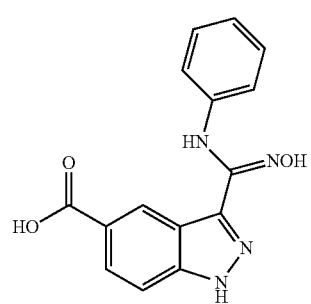
Formula 26
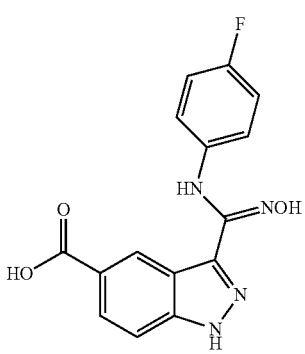
Formula 27
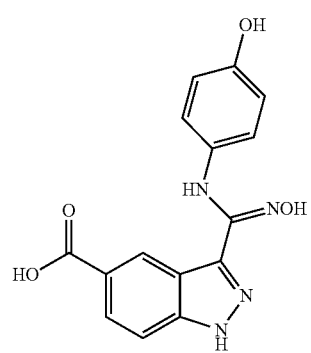
Formula 28
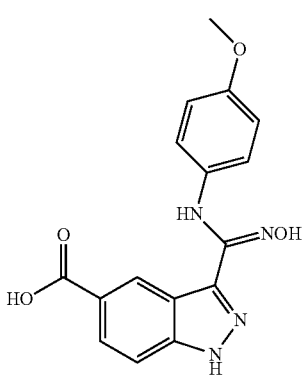
Formula 29
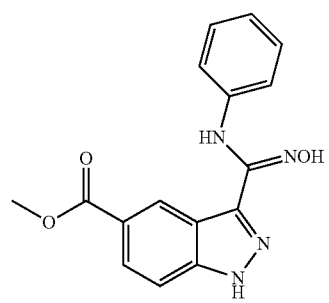
Formula 30
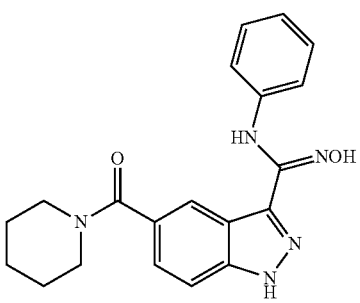

-continued
Formula 31
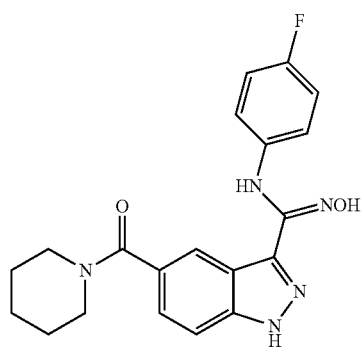
Formula 32
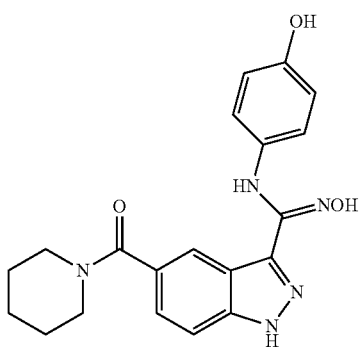
Formula 33
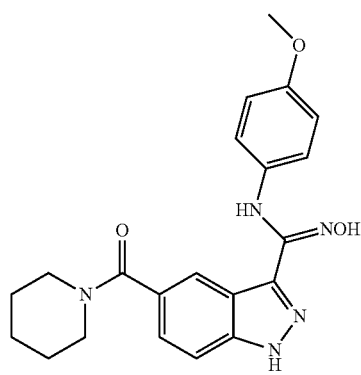
Formula 34
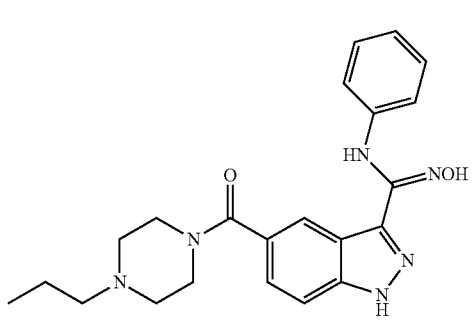
Formula 35
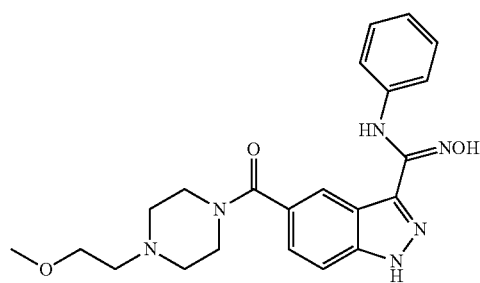
Formula 36
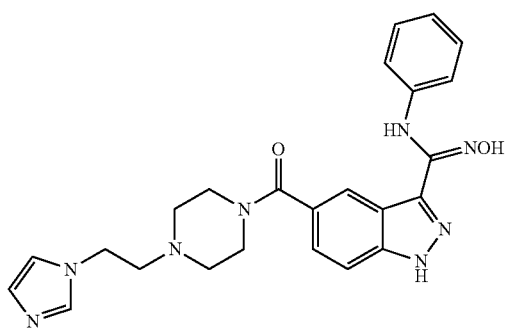
Formula 37
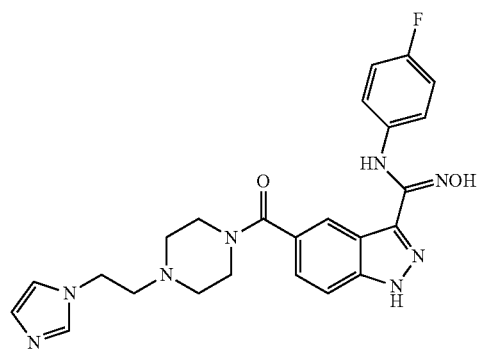
Formula 38
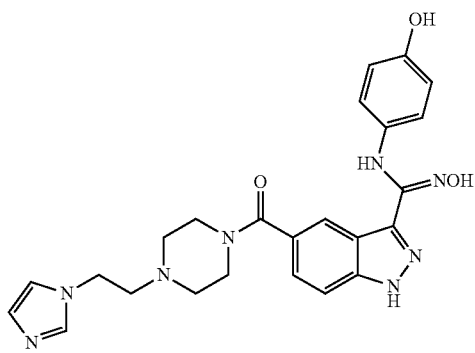

-continued
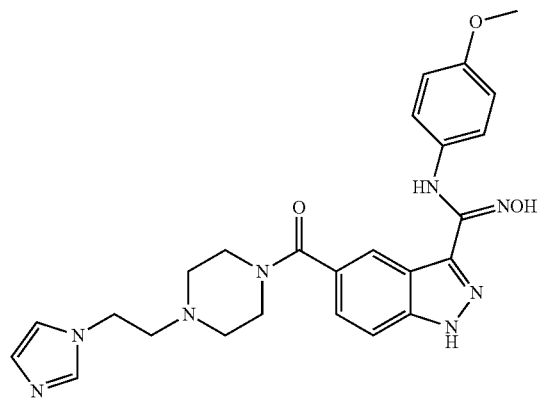
Formula 39
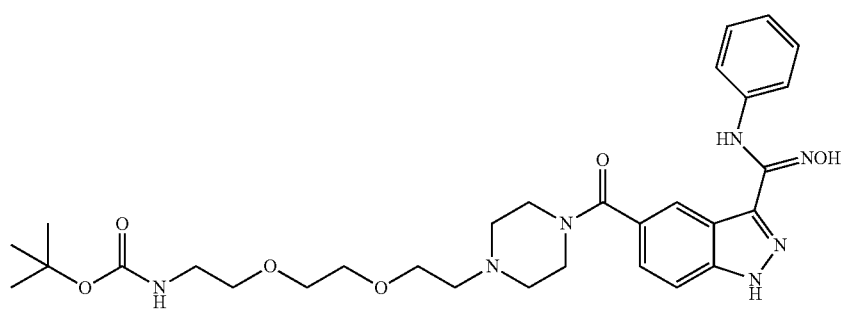
Formula 40
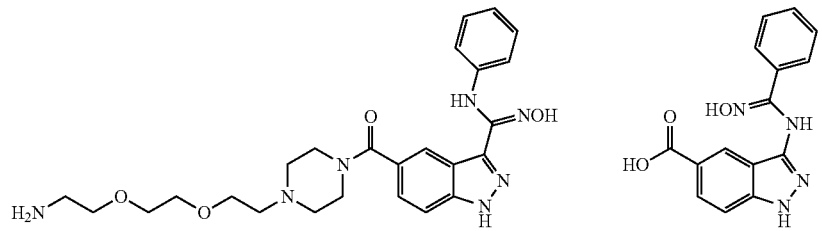
Formula 41
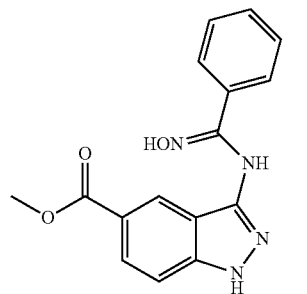
Formula 42
Formula 43
Formula 44
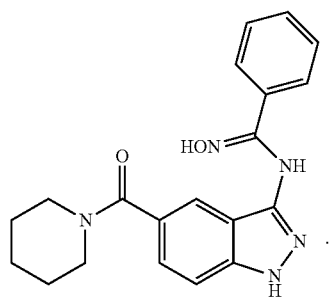
Formula 45

According to the present invention, the indazole derivative compound according to the present invention is represented by a formula selected from the group consisting of the following formula 1, formula 25, formula 30, formula 31, formula 33, formula 34, formula 35 and formula 45:

Formula 1

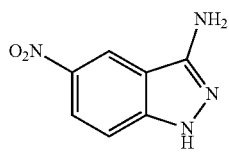

Formula 25

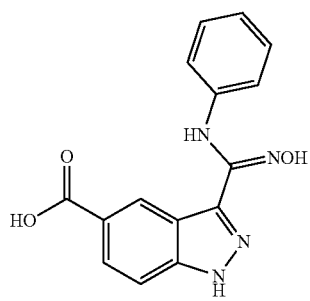

Formula 30

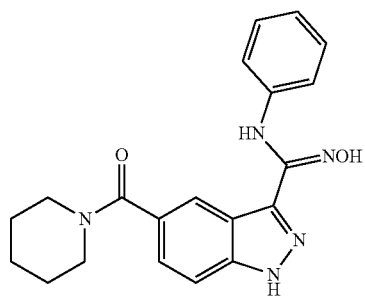

Formula 31

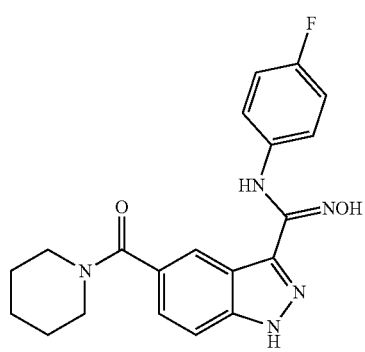

Formula 33

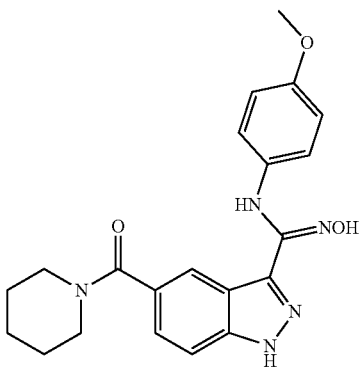

Formula 34

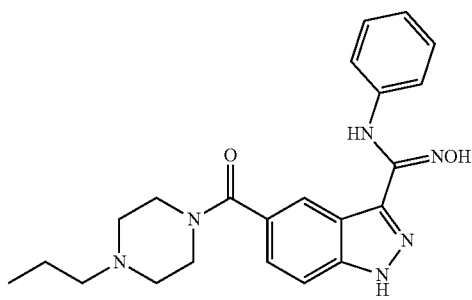

Formula 35

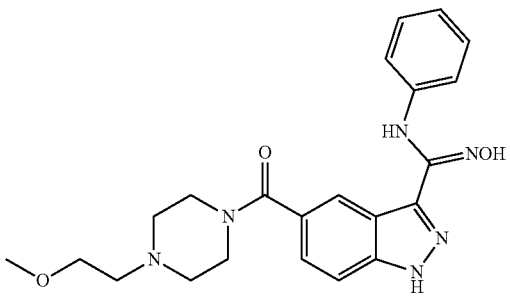

Formula 45

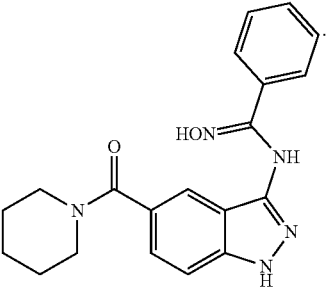

According to still another aspect, the present invention provides a method for inducing cell programming, comprising bringing a compound represented by the following formula A into contact with cells:

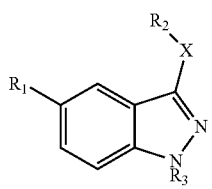

Formula A wherein $R_1$ is hydrogen, nitro, nitroxy or Y-carbonyl, wherein Y is hydrogen, hydroxy, halo, $C_{1-30}$ alkoxy, $C_{2-30}$ heterocycloalkyl containing nitrogen, oxygen or sulfur as a heteroatom, $C_{2-20}$ heterocycloalkenyl containing nitrogen, oxygen or sulfur as a heteroatom, $C_{6-30}$ aryl, $C_{1-30}$ alkyl, or $C_{2-30}$ alkenyl; $R_2$ is hydrogen, hydroxy, halo, $C_{1-30}$ aryl, $C_{1-30}$ alkoxy, $C_{1-30}$ alkyl, or $C_{2-30}$ alkenyl; $R_3$ is hydrogen, hydroxy, halo, $C_{1-30}$ aryl, $C_{1-30}$ alkoxy, $C_{1-30}$ alkyl, or $C_{2-30}$ alkenyl; and X is amine, amido, sulfonamido, carbonyl, oxime, or imidamido.

The method for inducing cell reprogramming according to the present invention is performed using the composition for inducing cell reprogramming according to the present invention as described above, and the common descriptions between the two are omitted in order to avoid undue redundancy leading to the complexity of the specification.

Advantageous Effects

The features and advantages of the present invention are summarized as follows:
(a) The present invention relates to a composition for inducing cell reprogramming.
(b) Indazole derivative compounds according to the present invention can perform efficient cell reprogramming while showing improved biological profiles.
(c) Indazole derivative compounds according to the present invention show no cytotoxicity, unlike conventional low-molecular compounds (e.g., Reversine or BIO) for inducing cell reprogramming. Thus, when these compounds are clinically applied, they can make a great contribution to the marker of cell therapeutic agents or cell reprogramming inducers.
(d) Meanwhile, conventional indazole derivative compounds are not known to be used for cell reprogramming, and cannot be used at high concentrations due to their nonspecific cytotoxicity.
(e) The compounds of the present invention have excellent cell reprogramming ability while causing little or no cytotoxicity, and have a new mechanism of action, compared to conventional indazole derivative compounds.

MODE FOR INVENTION

Figure 1:
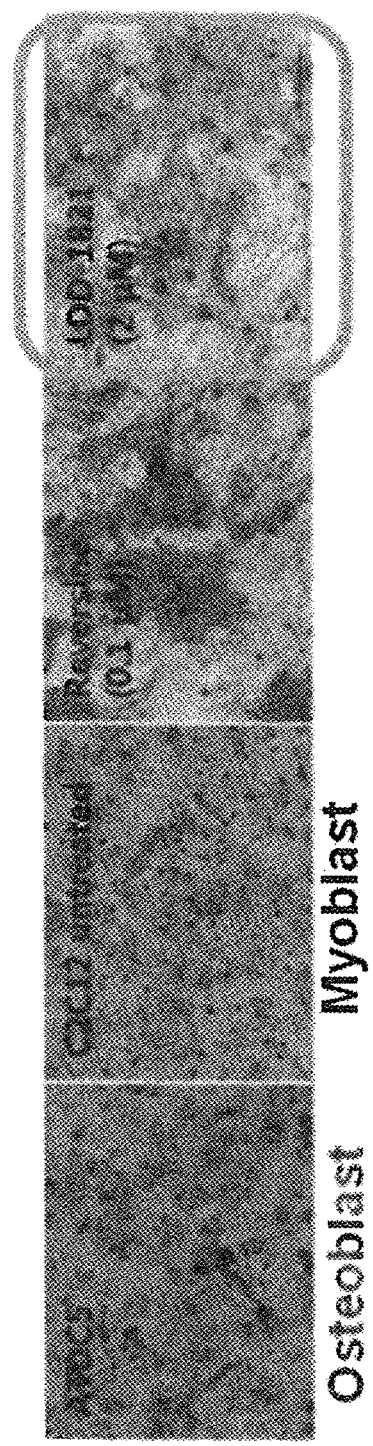
FIGS. 1 and 2 show the results of reprogramming C2C12 mouse myoblasts into osteoblasts by brining the myoblasts into contact with the compound of the present invention. The cells were brought into contact with LDD-1821, LDD-1664, LDD-1945, LDD-2199 or LDD-2200, which is the compound of the present invention, and then the cells were observed by Alizarin red staining (ATDC5: osteochondroprogenitor cell line).

Hereinafter, the present invention will be described in further detail with reference to examples. It will be obvious to those skilled in the art these examples are for illustrative purposes only and are not intended to limit the scope of the present invention.

SYNTHETIC EXAMPLES

Synthetic Scheme 1

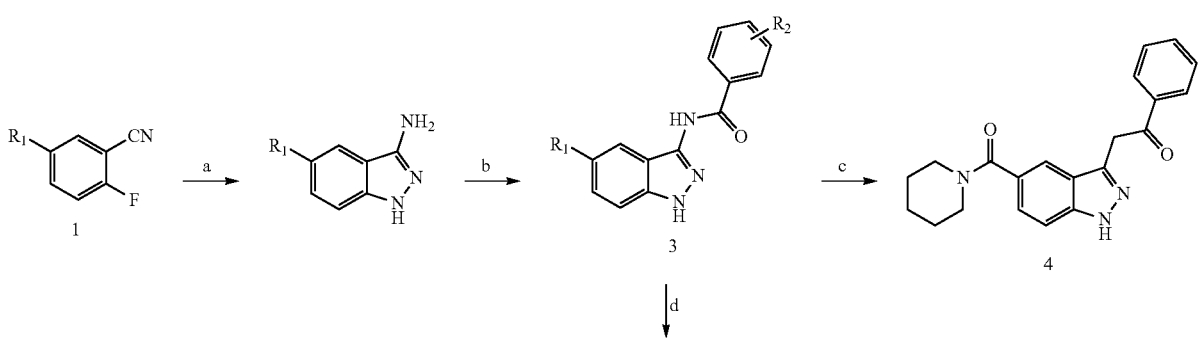

-continued

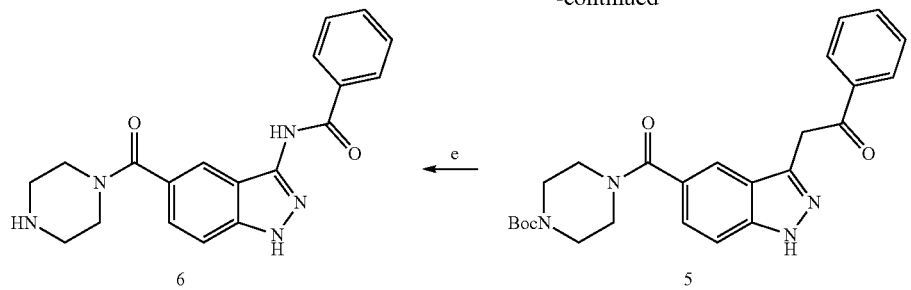

Reagents and conditions: a) hydrazinehydrate, 1-butanol, 110° C., 3h; b) R₂-benzoyl chloride, pyridine, rt, 5h; c) piperidine, EDC, HCl, DMAP, DCM, rt, 2h; d) t-butyl 4-aminopiperidine-1-carboxylate, EDC, HCl, DMAP, DCM, rt, 2h; e) TFA, MC, 0° C., 1h The reaction procedures and substituents described in the following synthetic examples refer to those shown in synthetic scheme 1 above.

General Synthetic Procedures

General Procedure of Step (a)

A starting material (1.0 g, 6.02 mmol) was dissolved in n-butanol (20 mL). Then, hydrazine hydrate (420 µL, 7.22 mmol) was added to the solution. The mixture was stirred at 110° C. for 2 hours and cooled, and then methylene chloride (MC) was added to the reaction mixture, and the formed precipitate was filtered, thereby obtaining the desired compound.

Synthetic Example 1: 5-nitro-1H-indazol-3-yl amine (Compound 1)

2-fluoro-5-nitrobenzonitrile (1.0 g, 6.02 mmol) was dissolved in n-butanol (20 mL). Then, hydrazine hydrate (420 µL, 7.22 mmol) was added to the solution. The mixture was stirred at 110° C. for 2 hours and cooled, and then methylene chloride (MC) was added to the reaction mixture, and the formed precipitate was filtered, thereby obtaining the desired compound (84% yield).

$^1$H NMR (400 MHz, DMS0-d6) δ 8.89 (d, 1H), 8.05 (dd, 1H), 7.34 (d, 2H), 5.98 (s, 2H). Mass=178.15.

Synthetic Example 2: 3-amino-1H-indazole-5-carboxylic Acid (Compound 2)

3-cyano-4-fluorobenzoic acid (1.0 g, 6.02 mmol) was dissolved in n-butanol (20 mL). Then, hydrazine hydrate (420 µL, 7.22 mmol) was added to the solution. The mixture was stirred at 110° C. for 2 hours and cooled, and then methylene chloride (MC) was added to the reaction mixture, and the formed precipitate was filtered, and then washed with MeOH, thereby obtaining the desired compound (55% yield).

$^1$H NMR (400 MHz, DMS0-d6) δ 11.35 (s, 1H), 8.45 (s, 1H), 7.80 (d, 2H), 7.22 (d, 1H), 5.59 (s, 2H). Mass=177.16.

General Procedure of Step (b-2)

The compound (50 mg, 0.28 mmol) of formula 2 in synthetic scheme 1 was dissolved in pyridine (0.3 mL). Then, R₂-benzoyl chloride (16.5 µL, 0.28 mmol) was added to the solution which was then stirred for 1 hour, followed by extraction with ethyl acetate and 1N HCl. The combined organic layer was washed with brine, dried with anhydrous Na₂SO₄, concentrated in a vacuum, and then purified by chromatography, thereby obtaining the desired compounds (Compounds 3 to 6).

Synthetic Example 3 (LDD-1664): N-(5-nitro-1(2)H-indazol-3-yl)-benzamide (Compound 3)

5-Nitro-1H-indazol-3-yl amine (50 mg, 0.28 mmol) was dissolved in pyridine (0.3 mL). Then, benzoyl chloride (16.5 µL, 0.28 mmol) was added to the solution which was then stirred for 1 hour, followed by extraction with ethyl acetate and 1N HCl. The combined organic layer washed with brine, dried with anhydrous Na₂SO₄, and then concentrated in a vacuum. The concentrate was purified by column chromatography, thereby obtaining the desired compound (42% yield).

$^1$H NMR (400 MHz, DMSO-d₆) δ 8.95 (d, 1H), 8.22 (dd, 1H), 8.12 (m, 2H), 8.12 (m, 2H), 7.69 (m, 4H). Mass=282.26.

Synthetic Example 4 (LDD-1663): 3-bromo-N-(5-nitro-1H-indazol-3-yl)benzamide (Compound 4)

5-nitro-1H-indazol-3-yl amine (0.14 mmol) was dissolved in pyridine (0.4 mL). Then, 3-bromobenzoyl chloride (19 µL, 0.14 mmol) was added to the solution which was then stirred for 1 hour, followed by extraction with ethyl acetate and 1N HCl. Dichloromethane (DCM) and hexane were added to the extract to form a precipitate, followed by filtration, thereby obtaining the desired compound (37% yield).

$^1$H NMR (400 MHz, DMSO-d₆) δ 11.32 (s, 1H), 8.93 (d, 1H), 8.26 (s, 1H), 8.19 (dd, 1H). Mass=361.16.

Synthetic Example 5 (LDD-2348): 4-methoxy-N-(5-nitro-1H-indazol-3-yl)benzamide (Compound 5)

5-nitro-1H-indazol-3-yl amine (25 mg, 0.14 mmol) was dissolved in pyridine (0.3 mL). Then, 4-methoxybenzoyl chloride (24 mg, 0.14 mmol) was added to the solution which was then stirred for 1 hour, followed by extraction with ethyl acetate and 1N HCl. The combined organic layer was washed with brine, dried with anhydrous Na₂SO₄, and then concentrated in a vacuum. The concentrate was purified by column chromatography, thereby obtaining the desired compound (40% yield).

$^1$H NMR (400 MHz, DMSO-d₆) δ 8.93 (d, 1H), 8.20 (dd, 1H), 8.12 (d, 2H), 7.67 (d, 1H), 7.11 (d, 2H), 3.86 (s, 3H). Mass=312.28.

Synthetic Example 6 (LDD-1665): 3-Benzamido-1H-indazole-5-carboxylic Acid (Compound 6)

3-amino-1H-indazole-5-carboxylic acid (25 mg, 0.14 mmol) was dissolved in pyridine (0.5 mL). Next, Benzoyl chloride (16.5 µL, 0.14 mmol) was added to the solution which was then stirred for 1 hour, followed by extraction with ethyl acetate and 1N HCl. DCM was added to form a precipitate, followed by filtration, thereby obtaining the desired compound (31% yield).

$^1$H NMR (400 MHz, DMSO-$d_6$) δ 10.98 (s, 1H), 8.11 (d, 2H), 7.94 (dd, 1H), 7.66 (t, 1H), 7.58 (t, 3H). Mass=281.27.

General Procedure of Step (c-3)

The compound (25 mg, 0.14 mmol) of formula 3 in synthetic scheme 1 was dissolved in dimethylformamide (DMF, 1 mL). Next, dimethylaminopyridine (DMAP, 0.03 mmol), piperidine (0.17 mmol) and ethylene dichloride (EDC, 0.28 mmol) were added to the solution which was then stirred at room temperature for 3 hours. The resulting residue was extracted with ethyl acetate and water. Next, silica gel chromatography was performed, thereby obtaining the desired compound.

Synthetic Example 7 (LDD-1820): N-(5-(piperidine-1-carbonyl)-1H-indazol-3-yl)benzamide (Compound 7)

3-benzamido-1H-indazole-5-carboxylic acid (25 mg, 0.14 mmol) was dissolved in DMF (1 mL). DMAP (0.03 mmol), piperidine (0.17 mmol) and EDC (0.28 mmol) were added to the solution which was then stirred at room temperature for 3 hours. The resulting residue was extracted with ethyl acetate and water. Next, silica gel chromatography was performed, thereby obtaining the desired compound (33% yield).

$^1$H NMR (400 MHz, CDCl$_3$) δ 11.02 (s, 1H), 9.26 (s, 1H), 8.15 (s, 1H), 8.04 (d, 2H), 7.59 (m, 3H), 7.37 (d, 1H), 7.21 (d, 1H), 3.59 (m, 4H), 1.75 (m, 6H). Mass=348.41.

General Procedure of Step (d-4)

The compound (25 mg, 0.14 mmol) of formula 3 in synthetic scheme 1 was dissolved in DMF (1 mL). DMAP (0.03 mmol), t-butyl 4-aminpiperidine-1-carboxylate (0.17 mmol) and EDC (0.28 mmol) were added to the solution which was then stirred at room temperature for 3 hours. The resulting residue was extracted with ethyl acetate and water. Next, silica gel chromatography was performed, thereby obtaining the desired compound (33% yield).

Synthetic Example 8 (LDD-1690): tert-butyl 4-(3-benazmido 1H-indazole-5-carbonyl)piperazine-1-carboxylate (Compound 8)

3-benzamido-1H-indazole-5-carboxylic acid (25 mg, 0.14 mmol) was dissolved in DMF (1 mL). DMAP (0.03 mmol), t-butyl 4-aminopiperidine-1-carboxylate (0.17 mmol) and EDC (0.28 mmol) were added to the solution which was then stirred at room temperature for 3 hours. The resulting residue was extracted with ethyl acetate and water. Next, silica gel chromatography was performed, thereby obtaining the desired compound (33% yield).

$^1$H NMR (400 MHz, DMSO-$d_6$) δ 10.82 (s, 1H), 8.23 (s, 2H), 8.07 (d, 2H), 7.85 (d, 1H), 7.60 (m, 4H), 3.96 (m, 3H), 2.79 (m, 2H), 1.74 (m, 2H), 1.41 (m, 11H). Mass=449.51.

General Procedure of Step (e-5)

The compound (30 mg, 0.065 mmol) of formula 5 in synthetic scheme 1 was dissolved in DCM (0.7 mL). TFA (0.2 ml) was added to the solution at 0° C., followed by stirring at 0° C. for 30 minutes. The reaction solution was concentrated in a vacuum, and then purified by silica gel chromatography using ammonia-saturated chloroform and methanol, thereby obtaining the desired compound.

Synthetic Example 9 (LDD-1691): N-(5-(piperazine-1-carbonyl)-1H-indazol-3-yl)benzamide (Compound 9)

Tert-butyl 4-(3-benzamido 1H-indazole-5-carbonyl)piperazine-1-carboxylate (30 mg, 0.065 mmol) was dissolved in DCM (0.7 mL). Next, trifluoroacetic acid (TFA, 0.2 ml) was added to the solution at 0° C., followed by stirring at 0° C. for 30 minutes. The reaction solution was concentrated in a vacuum, and then purified by silica gel chromatography using ammonia-saturated chloroform and MeOH, thereby obtaining the desired compound (20% yield).

$^1$H NMR (400 MHz, DMSO-$d_6$) δ 10.86 (s, 1H), 8.40 (d, 1H), 8.24 (s, 1H), 8.07 (d, 2H), 7.85 (d, 1H), 7.63 (m, 4H). Mass=349.39.

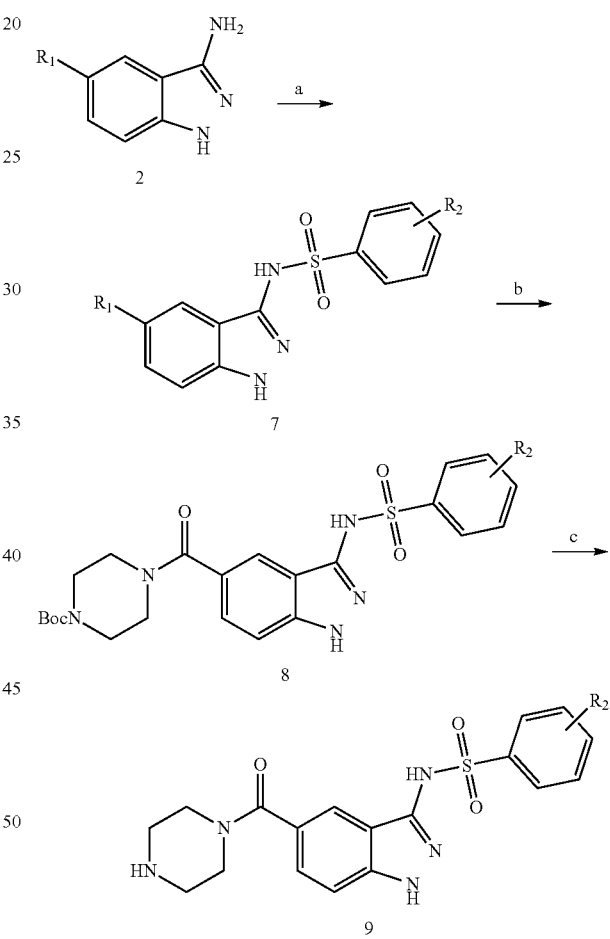

Synthetic Scheme 2

Reagents and conditions: a) benzensulfonyl chloride, pyridine, rt, 5h; b) t-butyl 4-aminopiperidine-4-carboxylate, EDC-HCl, DMAP, DCM, rt, 2h; c) TFA, DCM, 0° C., 1 h The reaction procedures and substituents described in the following synthetic examples refer to those shown in synthetic scheme 2 above.

General Synthetic Procedures

General Procedure of Step (a)

The compound (50 mg, 0.28 mmol) of formula 2 in synthetic scheme 2 was dissolved in pyridine (0.9 mL). Next, $R_2$-benzenesulfonyl chloride (36 µL, 0.28 mmol) was added to the solution which was then stirred for 1 hour, followed by extraction with ethyl acetate and 1N HCl. The combined organic layer was washed with brine, dried with anhydrous Na$_2$SO$_4$, and then concentrated in a vacuum. DCM was added to form a precipitate, followed by filtration, thereby obtaining the desired compound.

Synthetic Example 10 (LDD-1667): N-(5-nitro-1H-indazol-3-yl)benzenesulfonamide (Compound 10)

5-Nitro-1H-indazol-3-yl amine (50 mg, 0.28 mmol) was dissolved in pyridine (0.9 mL). Next, benzenesulfonyl chloride (36 μL, 0.28 mmol) was added to the solution which was then stirred for 1 hour, followed by extraction with acetate and 1N HCl. The combined organic layer was washed with brine, dried with anhydrous Na$_2$SO$_4$, and then concentrated in a vacuum. MC was added to form a precipitate, followed by filtration, thereby obtaining the desired compound (43% yield).
$^1$H NMR (400 MHz, DMSO-d$_6$) δ 11.14 (s, 1H), 8.70 (d, 1H), 8.12 (dd, 1H), 7.78 (d, 2H), 7.55 (m, 4H). Mass=318.31.

Synthetic Example 11 (LDD-1666): 3-bromo-N-(5-nitro-1H-indazol-3-yl)benzenesulfonamide (Compound 11)

5-Nitro-1H-indazol-3-yl amine (0.28 mmol) was dissolved in pyridine (0.9 mL). Next, 3-bromobenzenesulfonyl chloride (40 μL, 0.28 mmol) was added to the solution which was then stirred for 1 hour, followed by extraction with ethyl acetate and 1N HCl. DCM and hexane were added to the extract to form a precipitate, followed by filtration, thereby obtaining the desired compound (50% yield).
$^1$H NMR (400 MHz, DMSO-d$_6$) δ 10.99 (s, 1H), 8.72 (d, 1H), 8.19 (m, 1H), 7.99 (t, 1H), 7.87 (d, 1H), 7.81 (d, 1H), 7.63 (d, 1H), 7.54 (t, 1H). Mass=397.20.

Synthetic Example 12 (LDD-1668): 3-(phenylsulfonamido)-1H-indazole-5-carboxlic Acid (Compound 12)

3-Amino-1H-indazole-5-carboxylic acid (25 mg, 0.14 mmol) was dissolved in pyridine (0.7 mL). Benzenesulfonyl chloride (20 μL, 0.14 mmol) was added to the solution which was then stirred for 1 hour, followed by extraction with ethyl acetate and HCl. Methanol was added to the extract to form a precipitate, followed by filtration, thereby obtaining the desired compound (20% yield).
$^1$H NMR (400 MHz, DMSO-d$_6$) δ 10.88 (s, 1H), 8.42 (s, 1H), 7.89 (dd, 3H), 7.63 (m, 4H). Mass=317.32.

General Procedure of Step (b-2)

The compound (25 mg, 0.08 mmol) of formula 7 in synthetic scheme 2 was dissolved in DMF (0.8 mL). DMAP (0.02 mmol), t-butyl 4-aminopiperidine-1-carboxylate (0.09 mmol) and EDC (0.16 mmol) were added to the solution which was then stirred at room temperature for 3 hours. The resulting residue was extracted with ethyl acetate and water. Next, silica gel chromatography was performed, thereby obtaining the desired compound.

Synthetic Example 13 (LDD-1692): tert-butyl 4-(3-(phenylsulfonamido)-1H-indazole-5-carboxamido)piperidine-1-carboxylate (Compound 13)

3-(phenylsulfonamido)-1H-indazole-5-carboxylic acid (25 mg, 0.08 mmol) was dissolved in DMF (0.8 mL). DMAP (0.015 mmol), t-butyl 4-aminopiperidine-1-carboxylate (0.09 mmol) and EDC (0.16 mmol) were added to the solution which was then stirred at room temperature for 3 hours. The resulting residue was extracted with ethyl acetate and water. Next, silica gel chromatography was performed, thereby obtaining the desired compound (50% yield).
$^1$H NMR (400 MHz, DMSO-d$_6$) δ 10.77 (s, 1H), 8.31 (d, 2H), 7.83 (m, 3H), 7.62 (m, 1H), 7.57 (t, 2H), 7.44 (d, 1H). Mass=485.56.

General Procedure of Step (c-3)

The compound (20 mg, 0.038 mmol) of formula 8 in synthetic scheme 2 was dissolved in DCM (0.4 mL). TFA (0.15 ml) was added to the solution at 0° C., followed by stirring at 0° C. for 30 minutes. The reaction solution was concentrated in a vacuum, and then purified by silica gel chromatography using ammonia-saturated chloroform and MeOH, thereby obtaining the desired compound.

Synthetic Example 14 (LDD-1693): 3-(phenylsulfonamido)-N-(piperidin-4-yl)-1H-indazole-5-carboxamide (Compound 14)

Tert-butyl 4-(3-(phenylsulfonamido)-1H-indazole-5-carbonyl)piperazine-1-carboxylate (20 mg, 0.038 mmol) was dissolved in DCM (0.4 mL). Next, TFA (0.15 ml) was added to the solution at 0° C., followed by stirring at 0° C. for 30 minutes. The reaction solution was concentrated in a vacuum, and then purified by silica gel chromatography using ammonia-saturated chloroform and methanol, thereby obtaining the desired compound (20% yield).
$^1$H NMR (400 MHz, DMS0-d6) δ 11.92 (s, 1H), 8.28 (d, 1H), 8.22 (s, 1H), 7.80 (m, 2H), 7.68 (d, 1H), 7.38 (d, 3H), 7.20 (d, 1H), 3.95 (m, 1H), 3.16 (d, 3H), 2.78 (t, 2H), 1.85 (m, 2H), 1.57 (m, 2H). Mass=385.44.

Synthetic Scheme 3

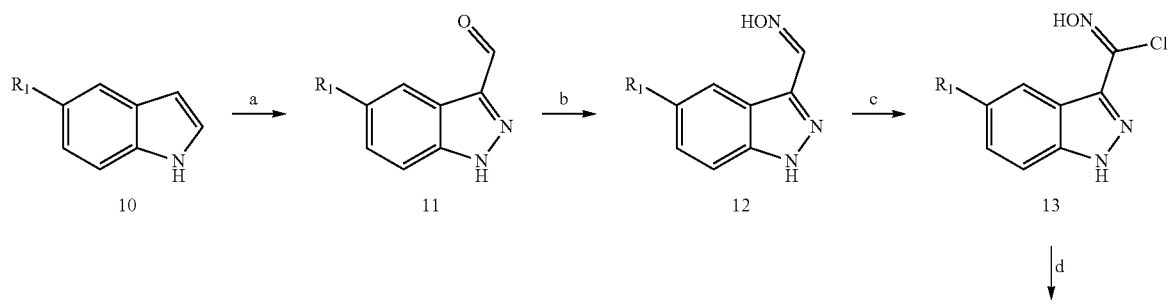

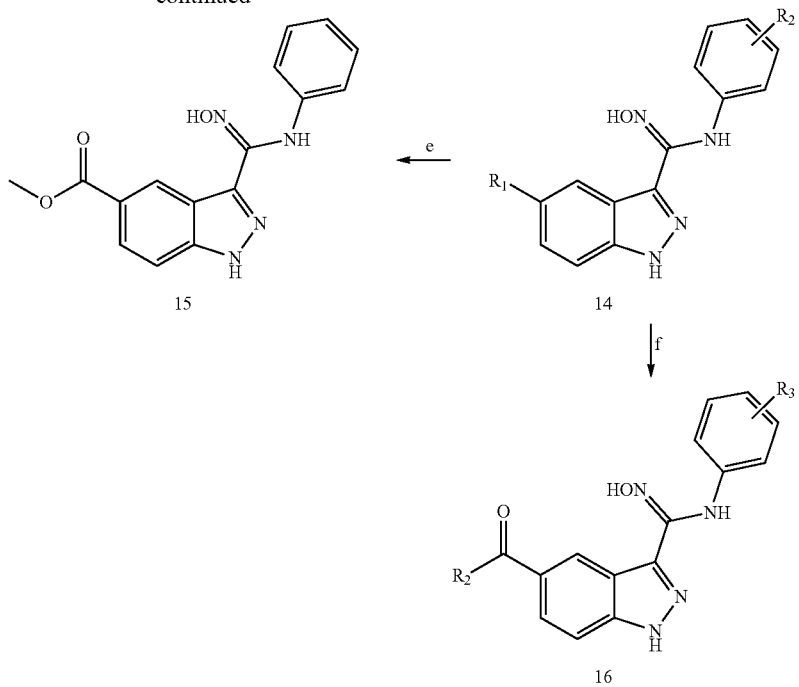

Reagents and conditions: a) sodium nitrite, HCl, water, rt, 8 h; b) hydroxylamine hydrochloride, TEA, DMF, 80° C., on; c) NCS, DMF, 40° C., 1 h; d) R₂-anine, TEA, 1.4-dioxane, rt, 1 h, e) TMS-diazomethane, DMF, 0° C., 30 min; f) various amine, EDC HCl, HOBt, DMF, rt, 1 h, The reaction procedures and substituents described in the following example refer to those shown in synthetic scheme 3 above.

General Synthetic Procedures

Synthetic Procedure of Step (a)

A starting material (1.0 g, 6.2 mmol) was added to water (40 ml), and a solution of sodium nitrite (4.3 g, 62 mmol) in water was added thereto. Next, 3N HCl was slowly added dropwise to the reaction mixture over 20 minutes. The reaction mixture was stirred at room temperature for 8 hours, and then the formed precipitate was filtered. The precipitate was completely dried, thereby obtaining the desired compound.

Synthetic Example 15: 5-nitro-1H-indazole-3-carbaldehyde (Compound 15)

5-Nitro-1H-indole (1.0 g, 6.2 mmol) was added to water (40 ml), and a solution of sodium nitrite (4.3 g, 62 mmol) in water was added thereto. Next, 3N HCl (21 ml) was slowly added dropwise to the reaction mixture over 20 minutes. The reaction mixture was stirred at room temperature for 8 hours, and then the formed precipitate was filtered. The precipitate was completely dried in a vacuum, thereby obtaining the desired compound (40% yield).

$^1$H NMR (400 MHz, DMSO-d$_6$) δ 11.98 (s, 1H), 9.75 (s, 1H), 8.87 (s, 1H), 8.56 (m, 2H). Mass=191.15.

Synthetic Example 16: 3-formyl-1H-indazole-5-carboxylic Acid (Compound 16)

$^1$H-indole-5-carboxylic acid (1.0 g, 6.02 mmol) was added to water (40 ml), and a solution of sodium nitrite (4.3 g, 62 mmol) in water was added thereto. Next, 3N HCl (21 ml) was slowly added dropwise to the reaction mixture over 20 minutes. The reaction mixture was stirred at room temperature for 8 hours, and then the formed precipitate was filtered. The precipitate was completely dried in a vacuum, thereby obtaining the desired compound (84% yield).

$^1$H NMR (400 MHz, DMSO-d6) δ 10.20 (s, 1H), 8.74 (s, 1H), 8.02 (d, 1H), 7.75 (d, 2H). Mass=190.16.

General Procedure of Step (b-2)

The compound (500 mg, 2.63 mmol) of the compound of formula 11 in synthetic scheme 3 was dissolved in DMF (13 mL). Next, hydroxylamine hydrochloride (550 mg, 7.89 mmol) and triethylamine (110 μL, 7.89 mmol) was added to the solution which was then stirred at 80° C. for 12 hours, followed by extraction with ethyl acetate and 1N HCl. The combined organic layer was washed with brine, dried with anhydrous Na₂SO₄, and then concentrated in a vacuum. The desired compound to be used in a subsequent reaction was obtained without separate purification.

Synthetic Example 17: 5-nitro-1H-idazole-3-carboxaldehyde oxime (Compound 17)

5-Nitro-1H-indazole-3-carbaldehyde (500 mg, 2.63 mmol) was dissolved in DMF (13 mL). Hydroxylamine hydrochloride (550 mg, 7.89 mmol) and triethylamine (110 μL, 7.89 mmol) were added to the solution which was then stirred at 80° C. for 12 hours, followed by extraction with ethyl acetate and 1N HCl. The combined organic layer was washed with brine, dried with anhydrous Na₂SO₄, and then concentrated in a vacuum. The desired compound to be used in a subsequent reaction was obtained without separate purification (93% yield).

¹H NMR (400 MHz, DMSO-d6) δ 11.98 (s, 1H), 11.12 (s, 1H), 8.87 (s, 1H), 8.56 (m, 2H), 7.95 (s, 1H). Mass=206.16.

Synthetic Example 18: 3-((hydroxyimino)methyl)-1H-indazole-5-carboxylic Acid (Compound 18)

3-Formyl-1H-indazole-5-carboxylic acid (500 mg, 2.63 mmol) was dissolved in DMF (13 mL). Hydroxylamine hydrochloride (550 mg, 7.89 mmol) and triethylamine (110 μL, 7.89 mmol) were added to the solution which was then stirred at 80° C. for 12 hours, followed by extraction with ethyl acetate and 1N HCl. The combined organic layer was washed with brine, dried with anhydrous $Na_2SO_4$, and then concentrated in a vacuum. The desired compound to be used in a subsequent reaction was obtained without separate purification (93% yield).

¹H NMR (400 MHz, DMSO-$d_6$) δ 11.61 (s, 1H), 8.75 (s, 1H), 8.38 (s, 1H), 7.96 (d, 2H), 7.62 (d, 1H). Mass=205.17.

General Procedure of Step (c-3)

The compound (500 mg, 2.44 mmol) of formula 12 in synthetic scheme 3 was dissolved in DMF (12 mL). Next, N-chlorosuccinimide (320 mg, 2.44 mmol) was added dropwise to the solution which was then stirred at 40° C. for 1 hour. The resulting residue was extracted with ethyl acetate and water. The combined organic layer was washed with brine, dried with anhydrous $NSO_4$, and then concentrated in a vacuum. The desired compound was obtained without separate purification.

Synthetic Example 19: N-hydroxy-5-nitro-1H-indazole-3-carbamimidoyl chloride (Compound 19)

5-Nitro-1H-indazole-3-carboxaldehyde oxime (500 mg, 2.44 mol) was dissolved in DMF (12 mL). N-chlorosuccinimide (320 mg, 2.44 mmol) was added to the solution which was then stirred at 40° C. for 1 hour. The resulting residue was extracted with ethyl acetate and water. The combined organic layer was washed with brine, dried with anhydrous $Na_2SO_4$, and then concentrated in a vacuum. The desired compound was obtained without separate purification (80% yield).

¹H NMR (400 MHz, DMSO-$d_6$) δ 11.98 (s, 1H), 11.12 (s, 1H), 8.87 (s, 1H), 8.56 (m, 2H). Mass=240.60.

Synthetic Example 20: 3-(chloro(hydroxyimino)methyl)-1H-indazole-5-carboxylic Acid (Compound 20)

3-((hydroxyimino)methyl)-1H-indazole-5-carboxylic acid (500 mg, 2.44 mmol) was dissolved in DMF (12 mL). N-chlorosuccinimide (320 mg, 2.44 mmol) was added to the solution which was then stirred at 40° C. for 1 hour. The resulting residue was extracted with ethyl acetate and water. The combined organic layer was washed with brine, dried with anhydrous $Na_2SO_4$, and then concentrated in a vacuum. The desired compound was obtained without separate purification (86% yield).

¹H NMR (400 MHz, DMSO-$d_6$) δ 10.98 (s, 1H), 8.78 (s, 1H), 7.99 (d, 1H), 7.68 (d, 1H). Mass=239.62.

General Procedure of Step (d-4)

The compound (30 mg, 0.13 mmol) of formula 13 in synthetic scheme 3 was dissolved in (1.5 mL). Next, $R_2$-aniline (35 μL, 0.38 mmol) was added to the solution which was then stirred at 80° C. for 2 hours. The resulting residue was concentrated to remove ethanol, and was then purified by silica gel chromatography, thereby obtaining the desired compound.

Synthetic Example 21 (LDD-2369): N'-hydroxy-5-nitro-N-phenyl-1H-indazole-3-carboxyimidamide (Compound 21)

N-hydroxy-5-nitro-1H-indazole-3-carbamimidoyl chloride (30 mg, 0.13 mmol) was dissolved in ethanol (1.5 mL). Aniline (35 μL, 0.38 mmol) was added to the reaction solution which was then stirred at 80° C. for 2 hours. The resulting residue was concentrated to remove ethanol, and was then purified by silica gel chromatography, thereby obtaining the desired compound (yield 33%).

¹H NMR (400 MHz, DMSO-$d_6$) δ 10.97 (s, 1H), 8.90 (d, 1H), 8.47 (s, 1H), 8.23 (dd, 1H), 7.75 (dd, 1H). Mass=297.27.

Synthetic Example 22 (LDD-2370): N-(4-fluorophenyl)-N'-hydroxy-5-nitro-1H-indazole-3-carboxyimidamide (Compound 22)

N-hydroxy-5-nitro-1H-indazole-3-carbamimidoyl chloride (30 mg, 0.13 mmol) was dissolved in ethanol (1.5 mL). Next, 4-fluoroaniline (37 μL, 0.38 mmol) was added to the reaction solution which was then stirred at 80° C. for 2 hours. The resulting residue was concentrated to remove ethanol, and was then purified by silica gel chromatography, thereby obtaining the desired compound (33% yield).

¹H NMR (400 MHz, DMSO-$d_6$) δ 10.95 (s, 1H), 8.92 (d, 1H), 8.49 (s, 1H), 8.23 (dd, 1H), 7.75 (dd, 1H), 6.94 (m, 2H), 6.75 (m, 2H). Mass=315.26.

Synthetic Example 23 (LDD-2371): N'-hydroxy-N-(4-hydroxyphenyl)-5-nitro-1H-indazole-3-carboxyimidamide (Compound 23)

N-hydroxy-5-nitro-1H-indazole-3-carbamimidoyl chloride (30 mg, 0.13 mmol) was dissolved in ethanol (1.5 mL). Next, 4-hydroxyaniline (41 mg, 0.38 mmol) was added to the reaction solution which was then stirred at 80° C. for 2 hours. The resulting residue was concentrated to remove ethanol, and was then purified by silica gel chromatography, thereby obtaining the desired compound (33% yield).

¹H NMR (400 MHz, DMSO-$d_6$) δ 10.65 (s, 1H), 8.92 (s, 1H), 8.84 (d, 1H), 8.21 (dd, 1H), 8.09 (s, 1H), 7.72 (d, 1H), 6.60 (m, 2H), 6.50 (m, 2H). Mass=313.27.

Synthetic Example 24 (LDD-2372): N'-hydroxy-N-(4-methoxyphenyl)-5-nitro-1H-indazole-3-carboxyimidamide (Compound 24)

N-hydroxy-5-nitro-1H-indazole-3-carbobamimidoyl chloride (30 mg, 0.13 mmol) was dissolved in ethanol (1.5 mL). Next, 4-methoxyaniline (41 mg, 47 mmol) was added to the reaction solution which was then stirred at 80° C. for 2 hours. The resulting residue was concentrated to remove ethanol, and was then purified by silica gel chromatography, thereby obtaining the desired compound (33% yield).

¹H NMR (400 MHz, DMSO-$d_6$) δ 10.74 (s, 1H), 8.87 (d, H), 8.23 (s, 1H), 8.21 (dd, 1H), 7.72 (d, 1H), 6.68 (m, 4H) Mass=327.30.

Synthetic Example 25 (LDD-1986): 3-(N'-hydroxy-N-phenylcarbamimidoyl)-1H-indazole-5-carboxylic Acid (Compound 25)

3-(chloro(hydroxyimino)methyl)-1H-indazole-5-carboxylic acid (30 mg, 0.13 mmol) was dissolved in ethanol (1.5 mL). Next, aniline (35 μL, 0.38 mmol) was added to the reaction solution which was then stirred at 80° C. for 2 hours. The resulting residue was concentrated to remove ethanol, and was then purified by silica gel chromatography, thereby obtaining the desired compound (75% yield).

$^1$H NMR (400 MHz, DMSO-d$_6$) δ 10.82 (s, 1H), 8.66 (s, 1H), 8.38 (s, 1H), 7.95 (dd, 1H), 7.60 (d, 1H), 7.07 (t, 2H), 6.78 (t, 1H), 6.69 (d, 2H). Mass=296.29.

Synthetic Example 26 (LDD-2197): 3-N-(4-fluorophenyl)-N'-hydroxycarbamimidoyl-1H-indazole-5-carboxylic Acid (Compound 26)

3-(Chloro(hydroxyimino)methyl)-1H-indazole-5-carboxylic acid (30 mg, 0.13 mmol) was dissolved in (1.5 mL). Next, 4-fluoroaniline (37 μL, 0.38 mmol) was added to the reaction solution which was then stirred at 80° C. for 2 hours. The resulting residue was concentrated to remove ethanol, and was then purified by silica gel chromatography, thereby obtaining the desired compound (29% yield).

$^1$H NMR (400 MHz, DMSO-d$_6$) δ 10.19 (s, 1H), 8.67 (s, 1H), 8.40 (s, 1H), 7.95 (dd, 1H), 7.60 (dd, 1H), 6.93 (m, 2H), 6.714 (m, 2H). Mass=314.28.

Synthetic Example 27 (LDD-2349): 3-(N'-hydroxy-N-(4-hydroxyphenyl)carbamimidoyl)-1H-indazole-5-carboxylic Acid (Compound 27)

3-(chloro(hydroxyimino)methyl)-1H-indazole-5-carboxylic acid (30 mg, 0.13 mmol) was dissolved in ethanol (1.5 mL). Next, 4-hydroxyaniline (41 mg, 0.38 mmol) was added to the reaction solution which was then stirred at 80° C. for 2 hours. The resulting residue was concentrated to remove ethanol, and was then purified by silica gel chromatography, thereby obtaining the desired compound (31% yield).

$^1$H NMR (400 MHz, DMSO-d$_6$) δ 13.23 (s, 1H), 10.45 (s, 1H), 8.93 (s, 1H), 8.90 (s, 1H), 7.92 (m, 2H), 7.47 (d, 1H), 6.64 (d, 2H), 6.40 (d, 2H). Mass=312.28.

Synthetic Example 28 (LDD-2198): 3-(N'-hydroxy-N-(4-methoxyphenyl)carbaminidoyl)-1H-indazole-5-carboxylic Acid (Compound 28)

3-(Chloro(hydroxyimino)methyl)-1H-indazole-5-carboxylic acid (30 mg, 0.13 mmol) was dissolved in ethanol (1.5 mL). Next, 4-methoxyaniline (41 mg, 47 mmol) was added to the reaction solution which was then stirred at 80° C. for 2 hours. The resulting residue was concentrated to remove ethanol, and was then purified by silica gel chromatography, thereby obtaining the desired compound (31% yield).

$^1$H NMR (400 MHz, DMS0-d$_6$) δ 10.60 (s, 1H), 8.59 (s, 1H), 8.11 (s, 1H), 7.89 (dd, 1H), 7.54 (dd, 1H), 6.61 (s, 4H), 3.58 (s, 3H). Mass=326.31.

General Procedure of Step (e-5)

The compound (10 mg, 0.02 mmol) obtained in Synthetic Example 25 was dissolved in DMF (0.3 mL). Next, tetramethylsilane (TMS)-diazomethane (100 μL) was slowly added dropwise to the solution at 0° C., followed by stirring at 0° C. for 30 minutes. The reaction solution was concentrated in a vacuum, and then purified by silica gel chromatography, thereby obtaining the desired compound.

Synthetic Example 29 (LDD-2196): Methyl-3-(N'-hydroxy-N-phenylcarbamimidoyl)-1H-indazole-5-carboxylate (Compound 29)

The compound (10 mg, 0.02 mmol) obtained in Synthetic Example 25 was dissolved in DMF (0.3 mL). Next, TMS-diazomethane (100 μL) was slowly added dropwise to the solution at 0° C., followed by stirring at 0° C. for 30 minutes. The reaction solution was concentrated in a vacuum, and then purified by silica gel chromatography, thereby obtaining the desired compound (83% yield).

$^1$H NMR (400 MHz, DMSO-d$_6$) δ 12.27 (s, 1H), 9.56 (dd, 1H), 9.20 (s, 1H), 8.65 (dd, 1H), 8.25 (dd, 1H), 7.54 (m, 2H), 7.19 (t, 1H), 7.06 (dd, 2H), 3.55 (s, 3H). Mass=310.31.

General Procedure of Step (f-6)

The compound (10 mg, 0.03 mmol) of formula 14 in synthetic scheme 3 was dissolved in DMF (0.3 mL). Next, hydroxybenzotriazole (HOBt, 0.04 mmol), piperidine (0.09 mmol), TEA (0.09 mmol) and EDC (0.09 mmol) were added to the reaction solution which was then stirred at room temperature for 3 hours. The resulting residue was extracted with ethyl acetate and saturated NH$_4$Cl aqueous solution. Next, purification was performed by silica gel chromatography, thereby obtaining the desired compound.

Synthetic Example 30 (LDD-1821): N'-hydroxy-N-phenyl-5-(piperidine-1-carbonyl)-1H-indazole-3-carboxamide (Compound 30)

The compound (10 mg, 0.03 mmol) of formula 14 in synthetic scheme 3 was dissolved in DMF (0.3 mL). Next, HOBt (0.04 mmol), piperidine (0.09 mmol), TEA (0.09 mmol) and EDC (0.09 mmol) were added to the reaction solution which was then stirred at room temperature for 3 hours. The resulting residue was extracted with ethyl acetate and saturated NH$_4$Cl aqueous solution. Next, purification was performed by silica gel chromatography, thereby obtaining the desired compound (65% yield).

$^1$H NMR (400 MHz, DMSO-d$_6$) δ 10.67 (s, 1H), 8.36 (s, 1H), 1.83 (s, 1H), 7.55 (d, 1H), 7.34 (d, 1H), 7.02 (t, 2H), 6.73 (t, 1H), 6.64 (d, 2H), 3.56 (m, 4H), 1.58 (m, 6H). Mass=363.42.

Synthetic Example 31 (LDD-2199): N-(4-fluorophenyl)-N'-hydroxy-5-(piperidine-1-carbonyl)-1H-indazole-3-carboxamide (Compound 31)

The compound (10 mg, 0.03 mmol) obtained in Example 26 was dissolved in DMF (0.3 mL). Next, HOBt (0.04 mmol), piperidine (0.09 mmol), TEA (0.09 mmol) and EDC (0.09 mmol) were added to the solution which was then stirred at room temperature for 3 hours. The resulting residue was extracted with ethyl acetate and saturated NH$_4$Cl aqueous solution. Next, purification was performed by silica gel chromatography, thereby obtaining the desired compound (72% yield).

$^1$H NMR (400 MHz, DMSO-d$_6$) δ 10.67 (s, 1H), 8.41 (s, 1H), 7.88 (s, 1H), 7.58 (dd, 1H), 7.38 (dd, 1H), 6.915 (m, 2H), 6.71 (m, 2H), 3.33 (m, 4H), 1.62 (m, 6H). Mass=381.41.

Synthetic Example 32 (LDD-2350): N'-hydroxy-N-(4-hydroxyphenyl)-5-(piperidine-1-carbonyl)-1H-indazole-3-carboxamide (Compound 32)

The compound (10 mg, 0.03 mmol) obtained in Example 27 was dissolved in DMF (0.3 mL). Next, HOBt (0.04 mmol), piperidine (0.09 mmol), TEA (0.09 mmol) and EDC (0.09 mmol) were added to the solution which was then stirred at room temperature for 3 hours. The resulting residue was extracted with ethyl acetate and saturated NH$_4$Cl aqueous solution. Next, purification was performed by silica gel chromatography, thereby obtaining the desired compound (65% yield).

¹H NMR (400 MHz, DMSO-d₆) δ 13.25 (s, 1H), 10.34 (s, 1H), 8.84 (s, 1H), 7.96 (s, 1H), 7.74 (s, 1H), 7.51 (d, 1H), 7.31 (dd, 1H), 6.53 (m, 2H), 6.44 (m, 2H), 3.39 (m, 4H), 1.60 (m, 6H). Mass=379.42.

Synthetic Example 33 (LDD-2200): N'-hydroxy-N-(4-methoxyphenyl)-5-(piperidine-1-carbonyl)-1H-indazole-3-carboxamide (Compound 33)

The compound (10 mg, 0.03 mmol) obtained in Example 28 was dissolved in DMF (0.3 mL). Next, HOBt (0.04 mmol), piperidine (0.09 mmol), TEA (0.09 mmol) and EDC (0.09 mmol) were added to the solution which was then stirred at room temperature for 3 hours. The resulting residue was extracted with ethyl acetate and saturated NH₄Cl aqueous solution. Next, purification was performed by silica gel chromatography, thereby obtaining the desired compound (41% yield).
¹H NMR (400 MHz, DMSO-d₆) δ 10.48 (s, 1H), 8.16 (s, 1H), 7.82 (s, 1H), 7.56 (dd, 1H), 7.36 (dd, 1H), 3.55 (s, 3H), 3.46 (m, 4H), 1.62 (m, 6H). Mass=393.45.

Synthetic Example 34 (LDD-1987): N'-hydroxy-N-phenyl-5-(4-propylpiperazine-1-carbonyl)-1H-indazole-3-carboxamide (Compound 34)

The compound (10 mg, 0.03 mmol) obtained in Example 25 was dissolved in DMF (0.3 mL). Next, HOBt (0.04 mmol), 1-propylpiperazine (0.09 mmol) and EDC (0.09 mmol) were added to the solution which was then stirred at room temperature for 3 hours. The resulting residue was extracted with ethyl acetate and water. Next, purification was performed by silica gel chromatography, thereby obtaining the desired compound (41% yield).
¹H NMR (400 MHz, DMSO-d) δ 10.69 (s, 1H), 8.37 (s, 1H), 7.87 (s, 1H), 7.59 (d, 1H), 1.39 (dd, 1H), 7.06 (t, 2H), 6.77 (t, 1H), 6.69 (d, 2H), 3.45 (m, 4H), 2.37 (m, 4H), 2.29 (t, 2H), 1.47 (q, 2H), 0.88 (m, 3H). Mass=406.49.

Synthetic Example 35 (LDD-1988): N'-hydroxy-5-(4-(2-methoxyethyl)piperazine-1-carbonyl)-N-phenyl-1H-indazole 3-carboximidamide (Compound 35)

The compound (10 mg, 0.03 mmol) obtained in Example 25 was dissolved in DMF (0.3 mL). Next, HOBt (0.04 mmol), 1-(2-methoxyethyl)piperazine (0.09 mmol) and EDC (0.09 mmol) were added to the solution which was then stirred at room temperature for 3 hours. The resulting residue was extracted with ethyl acetate and water. Next, purification was performed by silica gel chromatography, thereby obtaining the desired compound (36% yield).
¹H NMR (400 MHz, DMSO-d₆) δ 10.70 (s, 1H), 8.39 (s, 1H), 7.87 (s, 1H), 7.59 (d, 1H), 7.39 (dd, 1H), 7.06 (t, 2H), 6.77 (t, 1H), 6.69 (d, 2H), 3.46 (m, 6H), 3.24 (s, 1H), 2.52 (m, 2H), 2.40 (m, 4H). Mass=422.49.

Synthetic Example 36 (LDD-2351): 5-(4-(2-(1H-imidazol-1-yl)ethyl)piperazine-1-carbonyl)-N'-hydroxy-N-phenyl-1H-indazole-3-carboximidamide (Compound 36)

The compound (10 mg, 0.03 mmol) obtained in Example 25 was dissolved in DMF (0.6 mL). Next, HOBt (0.08 mmol), 1-(2-(1H-imidazol-1-yl)ethyl)piperazine (0.19 mmol) and EDC (0.19 mmol) were added to the solution which was then stirred at room temperature for 1 hour. The resulting residue was extracted with a solvent mixture of MC:MeOH=10:1 and a saturated NaHCO₃ aqueous solution. Next, purification was performed by silica gel chromatography using ammonia-saturated chloroform and methanol, thereby obtaining the desired compound (16% yield).
¹H NMR (400 MHz, DMSO-d₆) δ 10.74 (s, 1H), 8.37 (s, 1H), 7.870 (s, 1H), 7.65 (s, 1H), 7.58 (dd, 1H), 7.38 (dd, 1H), 7.20 (m, 1H), 7.05 (t, 2H), 6.87 (m, 1H), 6.77 (t, 1H), 6.68 (d, 2H), 4.10 (t, 2H), 3.46 (m, 4H), 2.68 (t, 2H), 2.42 (m, 4H). Mass=458.53.

Synthetic Example 37 (LDD-2352): 5-(4-(2-(1H-imidazol-1-yl)ethyl)piperazine-1-carbonyl)-N-(4-fluorpphenyl)-N'-hydroxy-1H-indazole-3-carboxyimidamide (Compound 37)

The compound (10 mg, 0.03 mmol) obtained in Example 25 was dissolved in DMF (0.6 mL). Next, HOBt (0.08 mmol), 1-(2-(1H-imidazol-1-yl)ethyl)piperazine (0.19 mmol) and EDC (0.19 mmol) were added to the solution which was then stirred at room temperature for 1 hour. The resulting residue was extracted with a solvent mixture of MC:MeOH=10:1 and a saturated NaHCO₃ aqueous solution. Next, purification was performed by silica gel chromatography using ammonia-saturated chloroform and methanol, thereby obtaining the desired compound (29% yield).
¹H NMR (400 MHz, DMS0-d₆) δ 10.74 (s, 1H), 8.42 (s, 1H), 7.90 (s, 1H), 7.65 (s, 1H), 7.58 (d, 1H), 7.39 (dd, 1H), 7.20 (t, 1H), 6.92 (m, 3H), 6.70 (m, 2H), 4.10 (t, 2H), 3.50 (m, 4H), 2.68 (t, 2H), 2.40 (m, 4H). Mass=476.52.

Synthetic Example 38 (LDD-2354): 5-(4-(2-(1H-imidazol-1-yl)ethyl)piperazine-1-carbonyl)-N'-hydroxy-N-(4-hydroxyphenyl)-1H-indazole-3-carboximidamide (Compound 38)

The compound (10 mg, 0.03 mmol) obtained in Example 25 was dissolved in DMF (0.6 mL). Next, HOBt (0.08 mmol), 1-(2-(1H-imidazol-1-yl)ethyl)piperazine (0.19 mmol) and EDC (0.19 mmol) were added to the solution which was then stirred at room temperature for 1 hour. The resulting residue was extracted with a solvent mixture of MC:MeOH=10:1 and a saturated NaHCO₃ aqueous solution. Next, purification was performed by silica gel chromatography using ammonia-saturated chloroform and methanol, thereby obtaining the desired compound (14% yield).
¹H NMR (400 MHz, DMSO-d₆) δ 13.29 (s, 1H), 10.41 (s, 1H), 8.88 (s, 1H), 7.99 (s, 1H), 7.79 (s, 1H), 7.71 (s, 1H), 7.55 (d, 1H), 7.36 (dd, 1H), 7.22 (m, 1H), 6.90 (m, 1H), 6.55 (m, 2H), 6.49 (m, 2H), 4.10 (t, 2H), 3.50 (m, 4H), 2.67 (t, 2H), 2.42 (m, 4H). Mass=474.52.

Synthetic Example 39 (LDD-2353): 5-(4-(2-(1H-imidazol-1-yl)ethyl) piperazine-1-carbonyl)-N'-hydroxy-N-(4-methoxyphenyl)-1H-indazole-3-carboximideamide (Compound 39)

The compound (10 mg, 0.03 mmol) obtained in Example 25 was dissolved in DMF (0.6 mL). Next, HOBt (0.08 mmol), 1-(2-(1H-imidazol-1-yl)ethyl)piperazine (0.19 mmol) and EDC (0.19 mmol) were added to the solution which was then stirred at room temperature for 1 hour. The resulting residue was extracted with a solvent mixture of MC:MeOH=10:1 and a saturated NaHCO₃ aqueous solution. Next, purification was performed by silica gel chromatography using ammonia-saturated chloroform and methanol, thereby obtaining the desired compound (31% yield).

$^1$H NMR (400 MHz, DMSO-$d_6$) δ 13.29 (s, 1H), 10.41 (s, 1H), 8.88 (s, 1H), 7.99 (s, 1H), 7.79 (s, 1H), 7.71 (s, 1H), 1.55 (d, 1H), 1.36 (dd, 1H), 1.22 (m, 1H), 6.90 (m, 1H), 6.55 (m, 2H), 6.49 (m, 2H), 4.10 (t, 2H), 3.50 (m, 4H), 2.67 (t, 2H), 2.42 (m, 4H). Mass=488.55.

Synthetic Example 40 (LDD-2319): tert-butyl (2-(2-(2-(4-(3-(N'-hydroxy-N-phenylcarbamimidoyl)-1H-indazole-5-carbonyl)piperazin-1-yl)ethoxy)ethoxy)ethyl)carbamate (Compound 40)

The compound (10 mg, 0.03 mmol) obtained in Example 25 was dissolved in DMF (0.6 mL). Next, HOBt (0.08 mmol), 1-(2-(1H-imidazol-1-yl)ethyl)piperazine (0.19 mmol) and EDC (0.19 mmol) were added to the solution which was then stirred at room temperature for 1 hour. The resulting residue was extracted with a solvent mixture of MC:MeOH=10:1 and a saturated NaHCO$_3$ aqueous solution. Next, purification was performed by silica gel chromatography using ammonia-saturated chloroform and methanol, thereby obtaining the desired compound (90% yield).

$^1$H NMR (400 MHz, DMSO-$d_6$) δ 10.68 (s, 1H), 8.36 (s, 1H), 7.82 (s, 1H), 7.53 (d, 1H), 7.33 (dd, 1H), 6.99 (t, 2H), 6.71 (m, 2H), 6.63 (d, 2H), 3.49 (m, 8H), 3.29 (m, 4H), 3.01 (m, 2H), 2.49 (m, 2H), 2.37 (m, 4H), 1.32 (s, 9H) Mass=595.7.

Synthetic Example 41 (LDEH2320): 5-(4-(2-(2-(2-aminoethoxy)ethoxy)ethyl)piperazine-1-carbonyl)-N'-hydroxy-N-phenyl-1H-indazole-3-carboximidamide (Compound 41)

The compound (10 mg, 0.02 mmol) obtained in Example 25 was dissolved in DCM (0.3 mL). Next, TFA (0.15 ml) was added to the solution at 0° C., followed by stirring at 0° C. for 30 minutes. The reaction solution was concentrated in a vacuum, and then purified by silica gel chromatography using ammonia-saturated chloroform and methanol, thereby obtaining (85% yield).

$^1$H NMR (400 MHz, DMSO-$d_6$) δ 10.75 (s, 1H), 8.40 (s, 1H), 7.86 (s, 1H), 7.57 (d, 1H), 7.38 (dd, 1H), 7.03 (t, 2H), 6.75 (t, 1H), 6.68 (d, 2H), 3.54 (m, 12H), 2.86 (m, 2H), 2.49 (m, 2H), 2.42 (m, 4H). Mass=495.58.

Synthetic Scheme 4

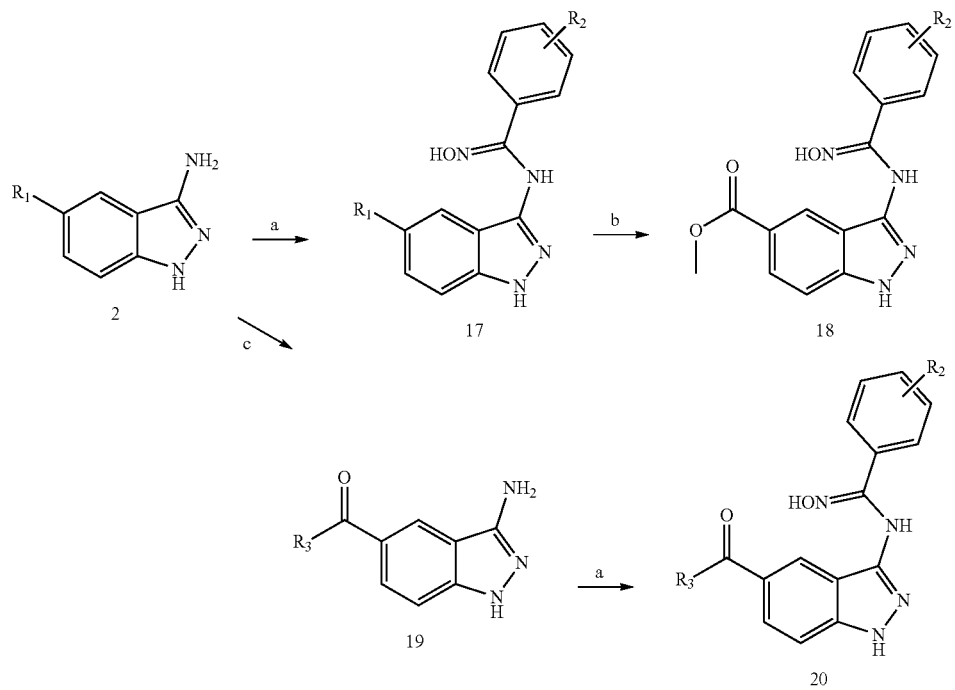

Reagents and conditions: a) R$_2$—N hydroxybenzimidoyl chloride, TEA, 1,4-dioxane, rt, o/n; b) TMS-diazomethene, DMF, 0° C., 30min; c) various amine, EDC-HCl, HOBt, DMF, rt 1h;

The reaction procedures and substituents described in the following synthetic examples refer to those shown in synthetic scheme 4 above.

General Synthetic Procedures

General Synthetic Procedure of Step (a)

The compound (20 mg, 0.11 mmol) of formula 2 in synthetic scheme 4 above was dissolved in 1,4-dioxane (1 mL). Then, R$_2$—N-hydroxybenzimidoyl chloride (0.17 mmol) and TEA (0.22 mmol) were added to the solution. The mixture was stirred at room temperature for 18 hours, and then the resulting residue was extracted with ethyl acetate and saturated NH$_4$Cl aqueous solution. Next, purification was performed by silica gel chromatography to afford the desired compound.

Synthetic Example 42 (LDD-2194): 3-(N'-hydroxy-benzimidamido)-1H-indazole-5-carboxylic Acid (Compound 42)

The compound (20 mg, 0.11 mmol) obtained in Synthetic Example 2 was dissolved in 1,4-dioxane (1 mL). Then, N-hydroxybenzimidoyl chloride (0.17 mmol) and TEA (0.22 mmol) were added to the solution. The mixture was stirred at room temperature for 18 hours, and then the resulting residue was extracted with ethyl acetate and saturated $NH_4Cl$ aqueous solution. Next, purification was performed by silica gel chromatography to afford the desired compound (23% yield).

$^1$H NMR (400 MHz, DMSO-$d_6$) δ 12.31 (s, 1H), 8.62 (m, 1H), 7.63 (dd, 1H), 7.43 (m, 3H), 7.33 (m, 2H), 7.16 (dd, 1H), 6.81 (s, 2H). Mass=296.29.

Synthetic Example 45 (LDD-1945): N'-hydroxy-N-(5-(piperidine-1-carbonyl)-1H-indazol-3-yl)benzimidamide (Compound 45)

The compound (10 mg, 0.04 mmol) obtained in Synthetic Example 44 was dissolved in 1,4-dioxane (0.4 mL). Then, N-hydroxybenzimidoyl chloride (0.04 mmol) and TEA (0.08 mmol) were added to the solution. The mixture was stirred at room temperature for 18 hours, and the formed precipitate was filtered, and washed with MC, thereby obtaining the desired compound (31% yield).

$^1$H NMR (400 MHz, DMSO-$d_6$) δ 12.28 (s, 1H), 7.91 (s, 1H), 7.43 (m, 3H), 7.32 (d, 2H), 7.18 (m, 2H), 6.48 (s, 2H), 3.57 (m, 4H), 1.54 (m, 6H). Mass=363.42.

General Procedure of Step (b-2)

The compound (10 mg, 0.03 mmol) of formula 17 in synthetic scheme 4 was dissolved in DMF (0.3 mL). Then, TMS-diazomethane (100 µL) was slowly added dropwise to the solution at 0° C., followed by stirring at 0° C. for 30 minutes. The reaction solution was concentrated in a vacuum, and then purified by silica gel chromatography to afford the desired compound.

Synthetic Example 43 (LDD-2195): Methyl-3-(N'-hydroxybenzimidamido)-1H-indazole-5-carboxylate (Compound 43)

The compound (10 mg, 0.03 mmol) obtained in Synthetic Example 42 was dissolved in DMF (0.3 mL). Then, TMS-diazomethane (100 µL) was slowly added dropwise to the solution at 0° C., followed by stirring at 0° C. for 30 minutes. The reaction solution was concentrated in a vacuum, and then purified by silica gel chromatography to afford the desired compound (85% yield).

$^1$H NMR (400 MHz, DMSO-$d_6$) δ 12.31 (s, 1H), 8.66 (m, 1H), 7.640 (dd, 1H), 7.43 (m, 3H), 7.33 (m, 2H), 7.19 (dd, 1H), 6.87 (s, 2H), 3.84 (s, 3H). Mass=310.31.

General Procedure of Step (c-3)

The compound (100 mg, 0.56 mmol) of formula 2 in synthetic scheme 2 was dissolved in DMF (2 mL). Next, HOBt (0.85 mmol), various amines (0.68 mmol), TEA (1.7 mmol) and EDC (1.13 mmol) were added to the solution which was then stirred at room temperature for 12 hours. The resulting residue was extracted with saturated $NaHCO_3$ aqueous solution and ethyl acetate. The combined organic layer was washed with brine, dried with anhydrous $Na_2SO_4$, and then concentrated in a vacuum. DCM and hexane were added to the concentrate to form a precipitate, followed by filtration, thereby obtaining the desired compound.

Synthetic Example 44: (3-amino-1H-indazol-5-yl)(piperidin-1-yl)methanone (Compound 44)

The compound (100 mg, 0.56 mmol) of formula 2 in formula 4 was dissolved in DMF (2 mL). Next, HOBt (0.85 mmol), various amines (0.68 mmol), TEA (1.7 mmol) and EDC (1.13 mmol) were added to the solution which was then stirred at room temperature for 12 hours. The resulting residue was extracted with saturated $NaHCO_3$ aqueous solution and ethyl acetate. The combined organic layer was washed with brine, dried with anhydrous $Na_2SO_4$, and then concentrated in a vacuum. DCM and hexane were added to the concentrate to form a precipitate, followed by filtration, thereby obtaining the desired compound (41% yield).

$^1$H NMR (400 MHz, DMSO-$d_6$) δ 11.58 (s, 1H), 7.81 (m, 1H), 7.24 (s, 2H), 5.50 (s, 2H), 3.40 (m, 4H), 1.61 (m, 6H). Mass=244.30.

EXPERIMENTAL EXAMPLES

Experimental Example 1: Cell Screening by Alizarin Red Staining

Screening of Low-Molecular Compounds That Induce Direct Cell Reprogramming

A method for identifying compounds that induce cell reprogramming was based on a previous study (PMID: 23044010 and 18974773) on the myocyte-to-osteocyte conversion by bone formation induction and a previous reversine publication (Chen S 2004).

C2C12 mouse skeletal myoblasts were seeded in a 24-well cell culture dish at a density of $1×10^4$ cells per well. 24 Hours after seeding, the compound of interest was added to three well at a concentration of 1. For a positive control, the cells were treated with 100 nM reversine or 2 µM BIO. The two compounds are known to induce the conversion of myoblasts to myocytes (Chen S 2004 and Kim WH recapitulate papers). For a negative control, the cells were untreated or treated with DMSO. The cells were treated with each compound for a total of 72 hours, and were further treated with each compound after 48 hours. The cytotoxicity of each compound could be confirmed from disappearance of a portion of the cells and from floating cell debris during culture, and a compound causing cytotoxicity was screened again at a concentration of 250 nM. After 72 hours, the medium was replaced with an osteogenic differentiation inducing medium (treated for 14 days with a DMEM supplemented with 10% FBS, 50 g/mL ascorbic acid-2-phosphate, 0.1 µM dexamethasone, 10 mM β-glycerophosphate, 50 units/mL of penicillin, and $50^{-1}$ streptomycin). The osteogenic differentiation inducing medium was based on one previously described in direct cell reprogramming (reversine papers, Chen S 2004 and Chen S 200/). Direct cell reprogramming from myocytes to osteocytes was analyzed by Alizarin red staining that detects calcium deposits (Gregory CA 2004 PMID: 15136169) in bone lineage cells.

Alizarin Red Staining

Cells were washed once with PBS, and then fixed with phosphate-buffered formalin for 20 minutes. The fixed cells were washed with distilled water, and immersed in a solution of 1% Alizarin red-S in water for 5 minutes. The remaining dye was washed out with distilled water. The cells were dried, and then imaged with an optical microscope (CKX41 Olympus). The stained cells did look red, and a compound corresponding to such cells was selected as a 'hit' compound and further analyzed.

Figure 2:
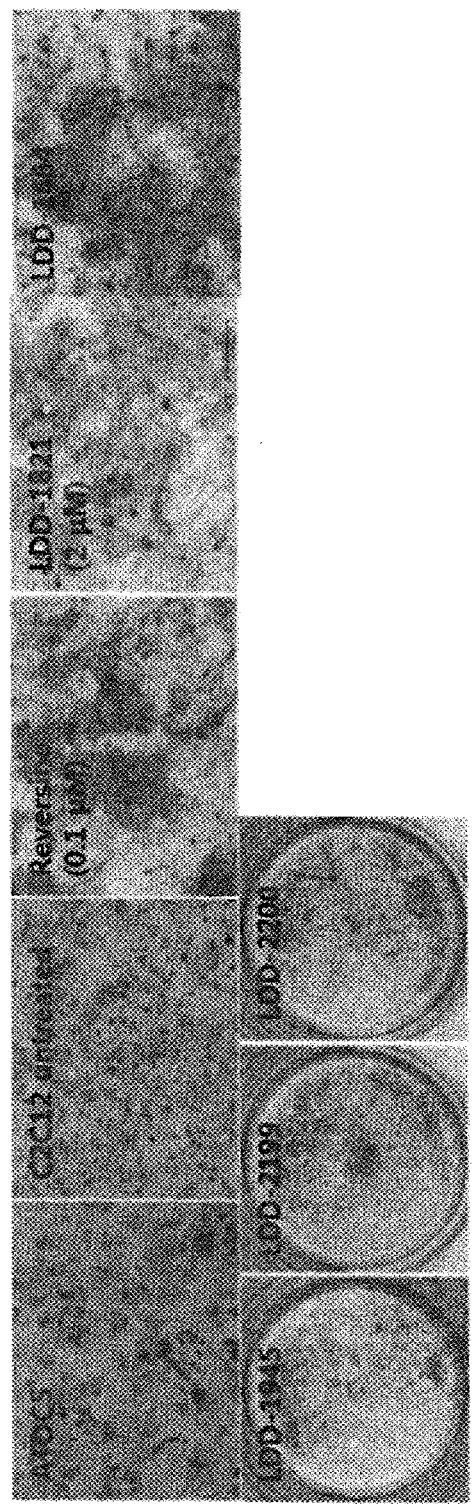
Figure 3:
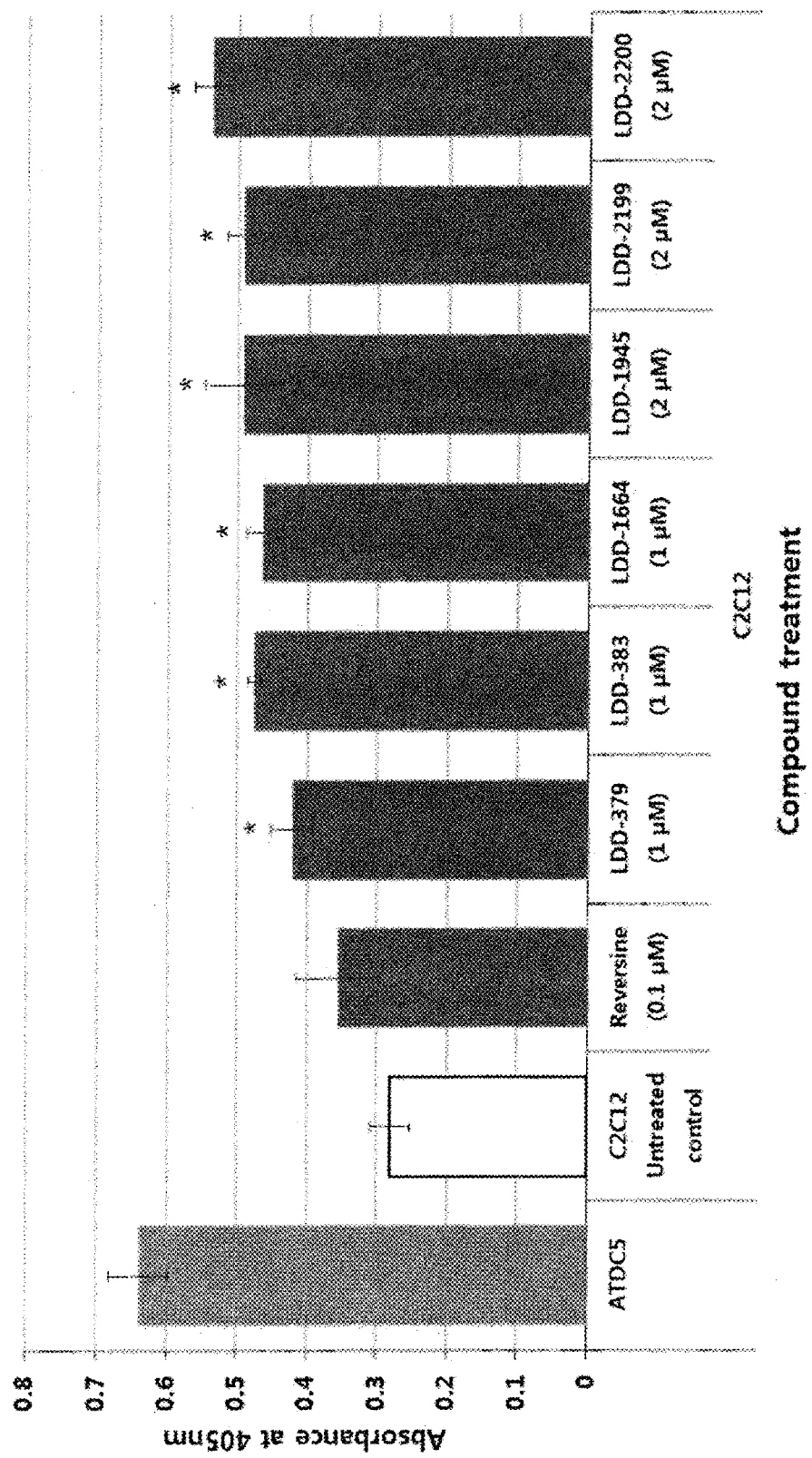
FIG. 3 shows the results obtained by brining C2C12 into contact with the compounds of the present invention and analyzing the cells by an Alizarin red assay. The graph shows absorbance measured after the cells were treated with each of the compounds.

Using the above-described assay method, the cell reprogramming potentials of the synthesized indazole compounds were evaluated. Compounds, LDD-1664, LDD-1821, LDD-1945, LDD-2199 and LDD-2200, showed a strong reprogramming potential in differentiation into osteoblasts, like the positive control reversine, and LDD-1986, LDD-1987 and LDD-1988 also showed reprogramming potential. In oil red O staining making it possible to observe differentiation into adipocytes, LDD-1821, LDD-1986, LDD-1987 and LDD-1988 compounds showed strong reprogramming potential. In particular, LDD-1821 showed strong reprogramming potential in differentiation into both osteoblasts and adipocytes (see FIGS. 1, 2 and 3).

TABLE 1

Cell staining results

| Compound | Alizarin red staining (osteoblasts) | Oil red O staining (adipocytes) |
|---|---|---|
| LDD-1664 | ++ | n.t |
| LDD-1667 | − | n.t |
| LDD-1820 | − | n.t |
| LDD-1821 | ++ | ++ |
| LDD-1986 | + | ++ |
| LDD-1987 | + | ++ |
| LDD-1988 | + | ++ |
| LDD-1945 | ++ | n.t |
| LDD-2199 | ++ | n.t |
| LDD-2200 | ++ | n.t |
| DMSO (−) | − | − |
| Reversine (+) | ++ | ++ |

++ (strong positive), + (weak positive), − (negative)

Experimental Example 2: Kinase Assay

The inhibitory activities of indazole derivatives against GSK-3 β and Aurora A were analyzed by HTRF (homogeneous time-resolved fluorescence) assay. The HTRF assay is an assay method that detects the phosphorylation of peptide substances in the presence of ATP. Phosphorylated substances were detected by TR-FRET (Time Resolved-Fluorescence Resonance) signals. Recombinant GSK-3 β and Aurora A kinase were purchased from Millipore (Billerica, Mass.). Using a HTRF KinEASE kit (Cisbio), the assay was performed. Each of GSK-3 β and Aurora A was treated with 1 μM of each indazole compound, and the degree of inhibition of phosphorylation was analyzed. The assay was composed of a compound-enzyme mixture and peptide substance dissolved in kinase reaction buffer (250 mM HEPES (pH 7.0), 0.5 mM orthovanadate, 0.05% BSA, 0.1% $NaN_3$). After addition of detection buffer, the TR-FRET signal was detected by an EnVision multi-label reader.

Table 2 below shows the degree of inhibition of enzymatic activities of GSK-3β and Aurora A by treatment with 1 μM of each of LDD-1664, LDD-1667, LDD-1820 and LDD-1821. As shown in Table 2, the four derivatives all showed an inhibitory activity of less than 50% against GSK-3 β and Aurora A at a concentration of 1 μM. In addition, LDD-1821 showing excellent reprogramming potential showed no inhibitory activity against the two enzymes at a concentration of 1 μM. Thus, it appears that the derivative compounds of the present invention induce cell reprogramming through mechanisms completely different from those of BIO and reversine, which are inhibitors of GSK-3β or Aurora A.

TABLE 2

Kinase assay

| Compound | Compound % Inhibition at 1 μM concentration | |
|---|---|---|
|  | GSK-3β | Aurora-A |
| LDD-1664 | 6.5 | 0 |
| LDD-1667 | 0 | 0 |
| LDD-1820 | 0.5 | 32.5 |
| LDD1821 | 0.2 | 0 |

Experimental Example 3: MTT Assay

Figure 4:
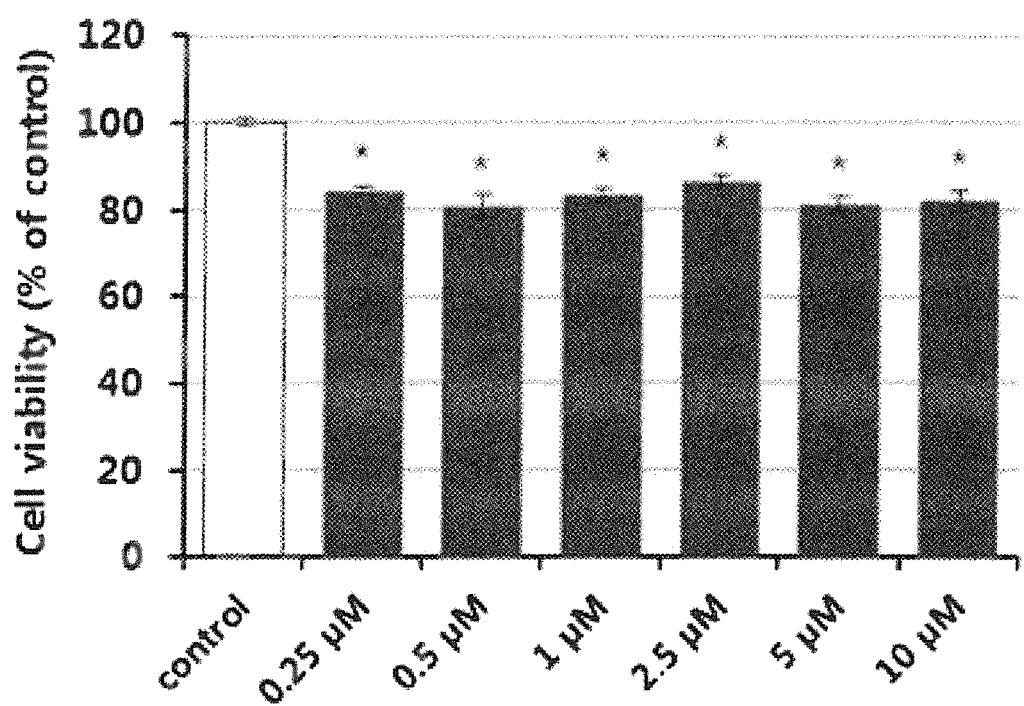
FIG. 4 shows the results of an MTT assay for C2C12 mouse myoblasts.

C2C12 myoblasts were seeded in a 96-well plate at a density of $3\times10^3$ cells per well. The cells were cultured for one day, and then treated with each compound. Next, the cells were incubated for 2 days, and then treated with a serum-free medium containing 3-(4,5-dimethylthiazol-2-yl)-2,5-diphenyltetrazolium bromide (MTT) for 3 hours. After removal of the medium, the cells were incubated in DMSO for 10 minutes while they were shaken. The absorbance at 570 nm was measured by a microreader (VersaMax, Molecular Devices) (see FIG. 4).

The cytotoxicities of compounds listed in Table 3 below were evaluated by the MTT assay. As a result, all the evaluated indazole derivatives showed an $IC_{50}$ of 10 μM or higher. In this respect, the indazole derivatives of the present invention have excellent advantages over conventional BIO and reversine which show high cytotoxicity.

TABLE 3

MTT assay results

| Compound | $IC_{50}$ (μM) |
|---|---|
| LDD-1821 | >10 |
| LDD-1986 | >10 |
| LDD-1987 | >10 |
| LDD-1988 | >10 |
| LDD-1945 | >10 |
| LDD-2194 | >10 |
| LDD-2195 | >10 |
| LDD-2196 | >10 |
| LDD-2197 | >10 |
| LDD-2198 | >10 |
| LDD-2199 | >10 |
| LDD-2200 | >10 |

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

The invention claimed is:

1. A compound represented by the following formula A as an indazole derivative:

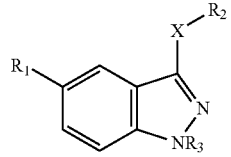

Formula A wherein

R$_1$ is nitroxy or Y-carbonyl, wherein Y is hydrogen, hydroxy, halo, C$_{1-30}$ alkoxy, C$_{2-30}$ heterocycloalkyl containing nitrogen, oxygen or sulfur as a heteroatom, C$_{2-20}$ heterocycloalkenyl containing nitrogen, oxygen or sulfur as a heteroatom, C$_{6-30}$ aryl, C$_{1-30}$ alkyl, or C$_{2-30}$ alkenyl;

R$_2$ is halo, C$_{1-30}$ aryl, or C$_{2-30}$ alkenyl;

R$_3$ is hydrogen, hydroxy, halo, C$_{1-30}$ aryl, C$_{1-30}$ alkoxy, C$_{1-30}$ alkyl, or C$_{2-30}$ alkenyl; and X is amine, amido, sulfonamido, carbonyl, oxime, or imidamido.

2. The compound of claim 1, wherein R$_1$ is Y-carbonyl, and Y is hydrogen, hydroxy, halo, C$_{1-15}$ alkoxy, C$_{2-15}$ heterocycloalkyl containing nitrogen, oxygen or sulfur as a heteroatom, C$_{2-15}$ heterocycloalkenyl containing nitrogen, oxygen or sulfur as a heteroatom, C$_{6-15}$ aryl, C$_{1-15}$ alkyl, or C$_{2-15}$ alkenyl.

3. The compound of claim 1, wherein R$_1$ is Y-carbonyl, Y is the heterocycloalkyl and the heterocycloalkyl in Y is substituted with hydroxy, halo, C$_{1-5}$ alkyl, C$_{2-5}$ alkenyl, C$_{1-5}$ alkoxy, C$_{2-8}$ alkoxyalkyl, C$_{2-8}$ alkoxycarbonyl, C$_{2-8}$ heterocycloalkenyl alkyl containing nitrogen as a heteroatom,

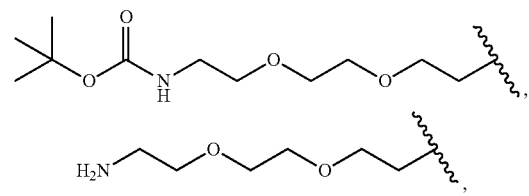

or a combination thereof.

4. The compound of claim 3, wherein the heterocycloalkenyl alkyl is (1H-imidazol-1-ly)alkyl.

5. The compound of claim 1, wherein R$_2$ is halo, C$_{1-15}$ aryl, or C$_{2-15}$ alkenyl.

6. The compound of claim 1, wherein the aryl in R$_2$ is substituted with hydroxy, halo, C$_{1-5}$ alkoxy, C$_{1-5}$ alkyl, C$_{2-5}$ alkenyl, or a combination thereof.

7. The compound of claim 1, wherein R$_1$ is Y-carbonyl, Y is heterocycloalkyl or heterocycloalkenyl, and the heteroatom is nitrogen.

8. A compound represented by a formula selected from the group consisting of the following formulas 6-9, 12-14, 18, 20 and 25-45:

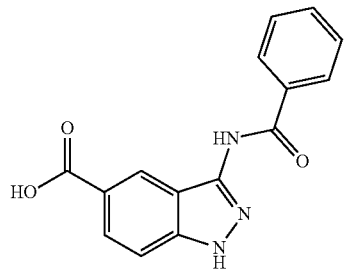

Formula 6

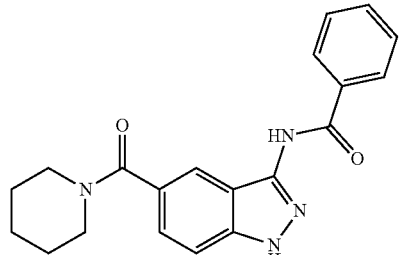

Formula 7

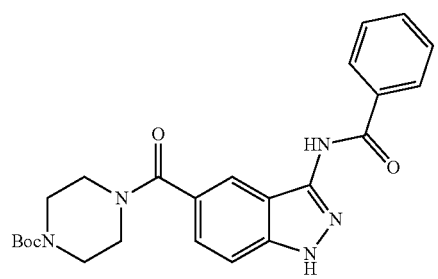

Formula 8

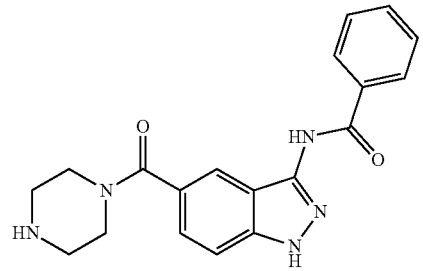

Formula 9

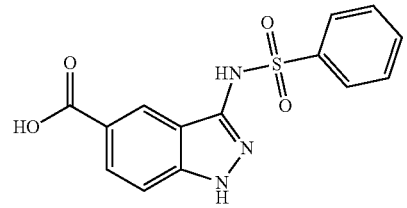

Formula 12

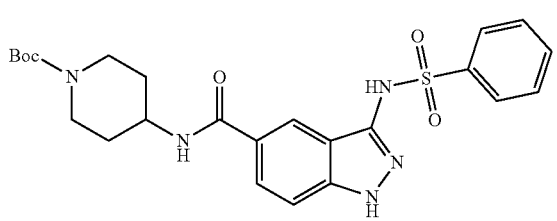

Formula 13

-continued
Formula 14
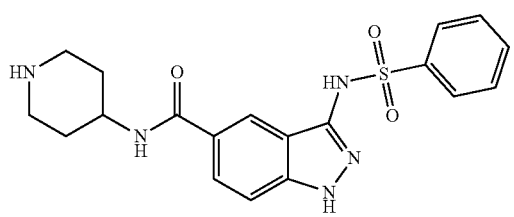
Formula 18
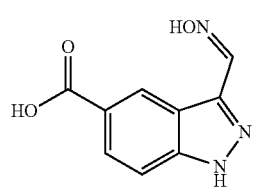
Formula 20
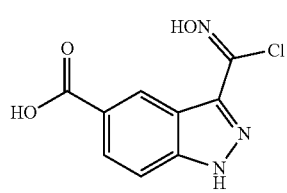
Formula 25
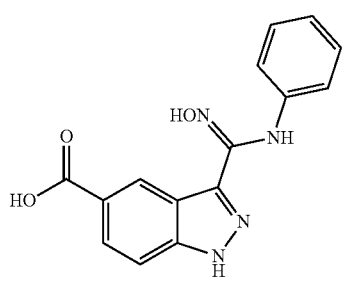
Formula 26
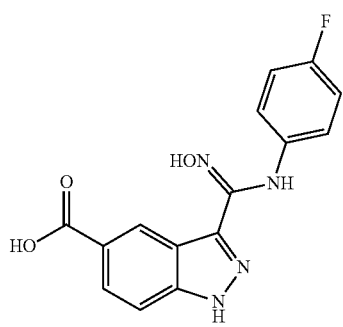
Formula 27
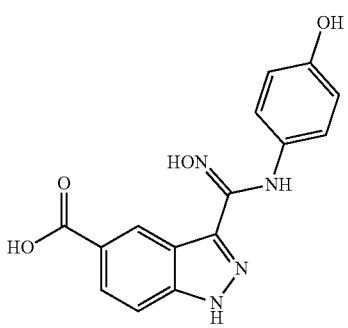
Formula 28
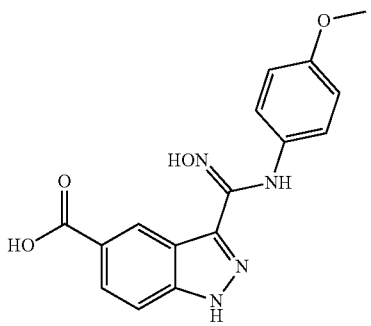
Formula 29
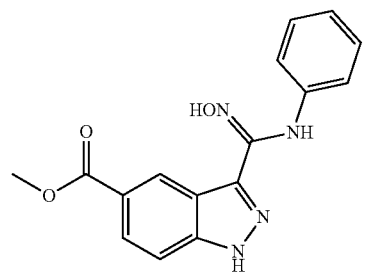
Formula 30
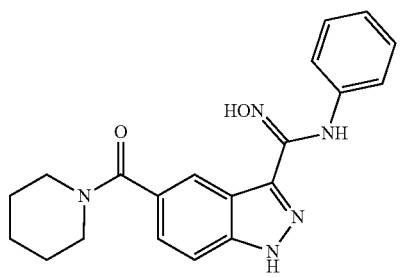
Formula 31
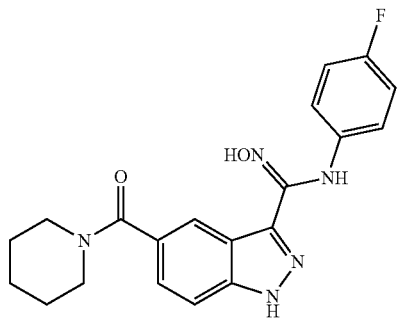
Formula 32
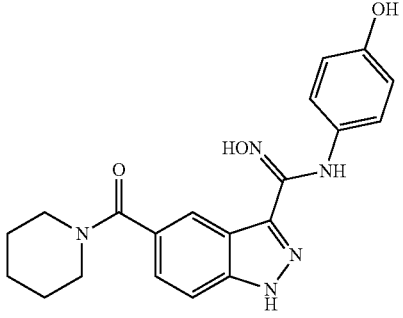

Formula 33
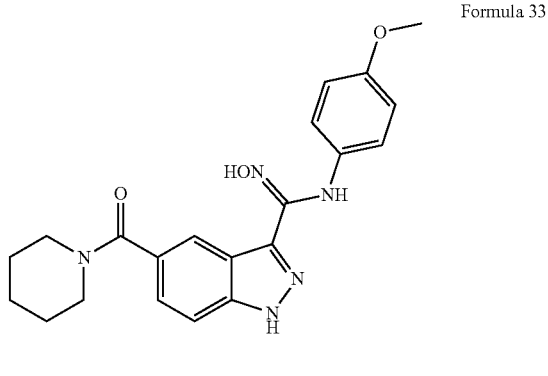
Formula 34
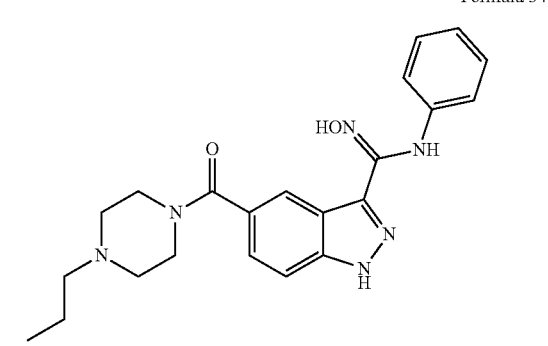
Formula 35
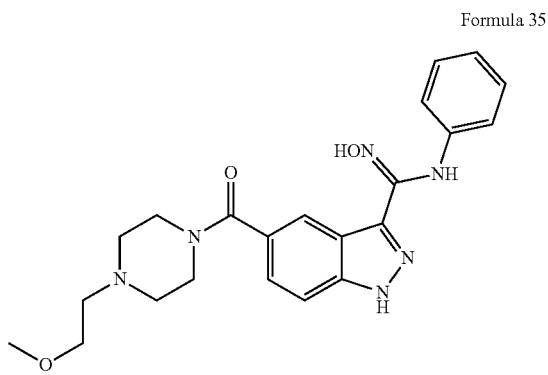
Formula 36
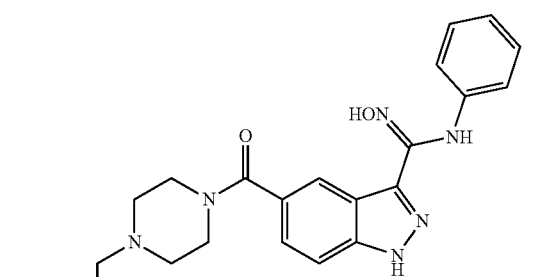
Formula 37
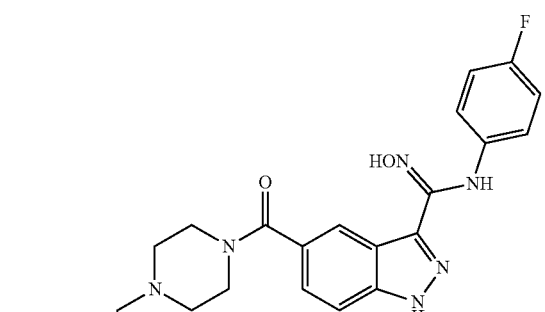
Formula 38
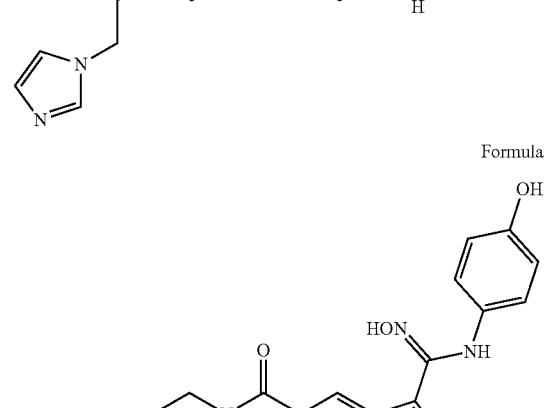
Formula 39
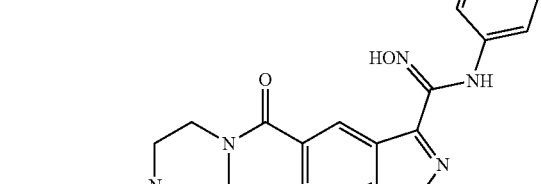
Formula 40
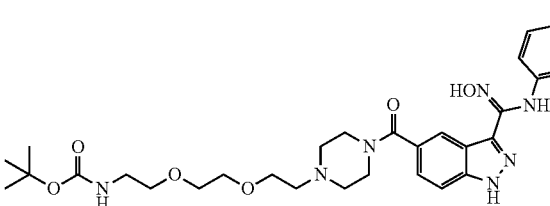

Formula 41
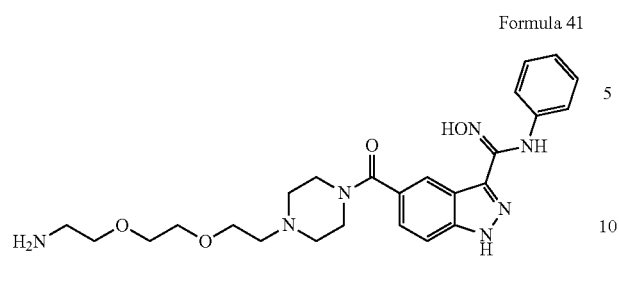
Formula 25
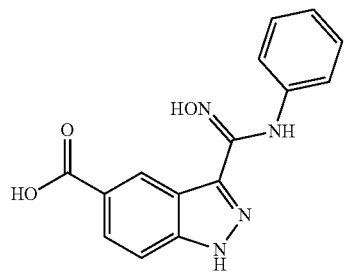
Formula 42
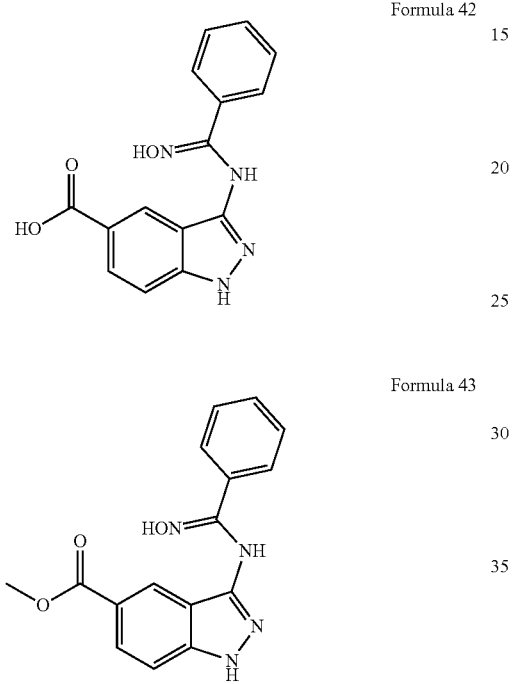
Formula 30
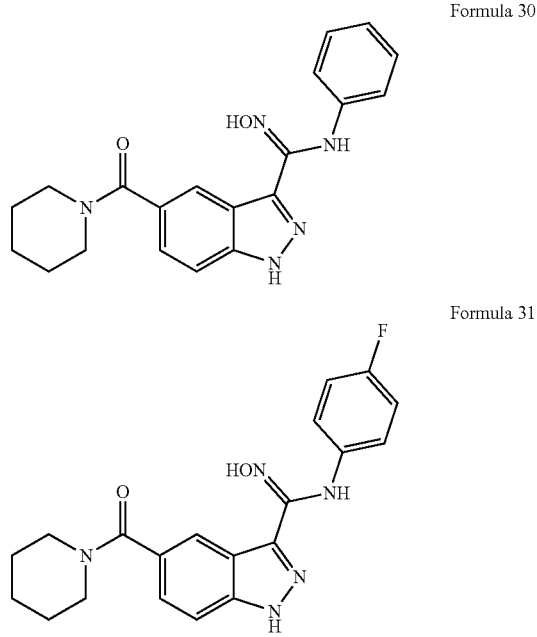
Formula 43
Formula 31
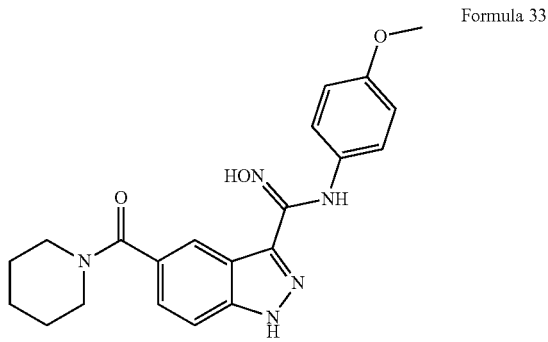
Formula 44
Formula 33
Formula 45
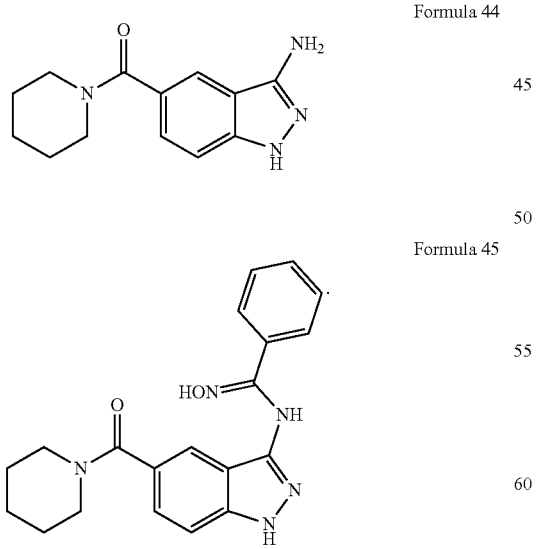
Formula 34
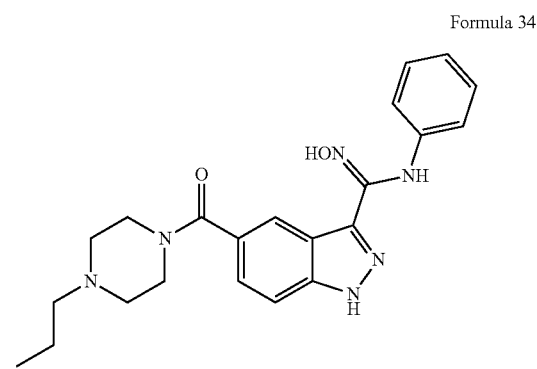
9. The compound of claim 8, wherein the compound is represented by a formula selected from the group consisting of the following formulas 25, 30, 31, 33, 34, 35 and 45:

-continued

Formula 35

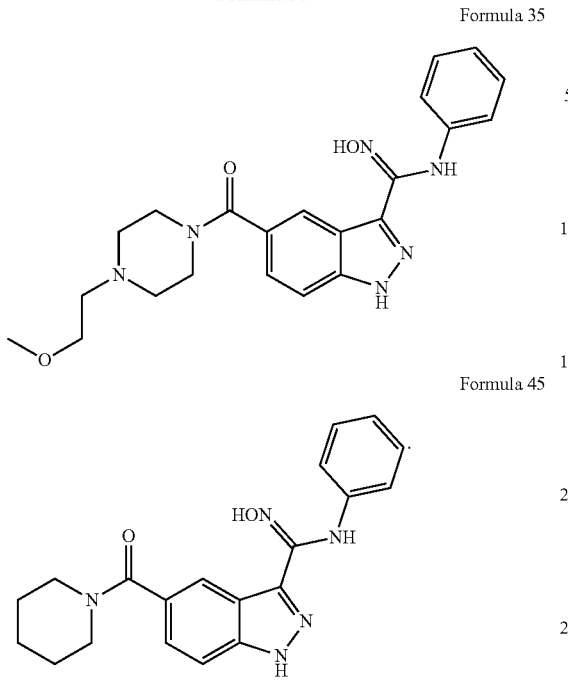

Formula 45

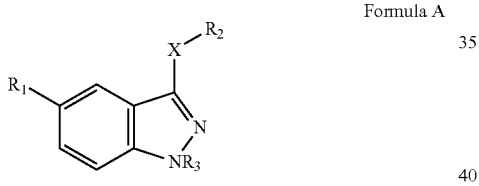

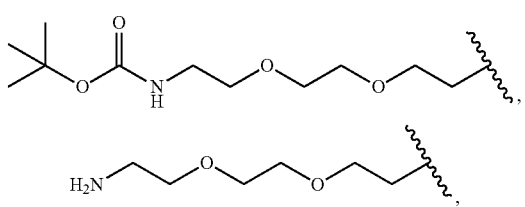

or a combination thereof.

13. The method of claim 10, wherein $R_2$ is hydrogen, halo, C1-15 aryl, C1-15 alkoxy, C1-15 alkyl, or C2-15 alkenyl.

14. The method of claim 10, wherein X in formula A is imidamido, and $R_2$ is bound to nitrogen of the imidamido.

15. The method of claim 10, wherein the compound is represented by a formula selected from the group consisting of the following formulas 1 to 45:

Formula 1

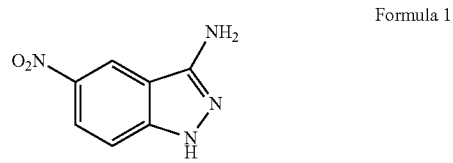

10. A method for inducing cell reprogramming, comprising bringing a composition comprising a compound represented by the following formula A into contact with cells:

Formula A $$\begin{array}{c} R_1 \overset{X-R_2}{\underset{NR_3}{\bigvee}} \end{array}$$

wherein $R_1$ is hydrogen, nitro, nitroxy or Y-carbonyl, wherein Y is hydrogen, hydroxy, halo, $C_{1-30}$ alkoxy, $C_{2-30}$ heterocycloalkyl containing nitrogen, oxygen or sulfur as a heteroatom, $C_{2-20}$ heterocycloalkenyl containing nitrogen, oxygen or sulfur as a heteroatom, $C_{6-30}$ aryl, $C_{1-30}$ alkyl, or $C_{2-30}$ alkenyl; $R_2$ is hydrogen, hydroxy, halo, $C_{1-30}$ aryl, $C_{1-30}$ alkoxy, $C_{1-30}$ alkyl, or $C_{2-30}$ alkenyl; $R_3$ is hydrogen, hydroxy, halo, $C_{1-30}$ aryl, $C_{1-30}$ alkoxy, $C_{1-30}$ alkyl, or $C_{2-30}$ alkenyl; and X is amine, amido, sulfonamido, carbonyl, oxime, or imidamido, wherein the cells are selected from mammalian myoblasts, and wherein the cells are induced to differentiated into osteogenic lineage or adipogenic lineage by the compound.

11. The method of claim 10, wherein $R_1$ is Y-carbonyl, and Y in $R_1$ is hydrogen, hydroxy, halo, C1-15 alkoxy, C2-15 heterocycloalkyl containing nitrogen, oxygen or sulfur as a heteroatom, C2-15 heterocycloalkenyl containing nitrogen, oxygen or sulfur as a heteroatom, C6-15 aryl, C1-15 alkyl, or C2-15 alkenyl.

12. The method of claim 10, wherein $R_1$ is Y-carbonyl, and Y in $R_1$ is the heterocycloalkyl, and the heterocycloalkyl in Y is substituted with hydroxy, halo, C1-5 alkyl, C2-5 alkenyl, C1-5 alkoxy, C2-8 alkoxyalkyl, C2-8 alkoxycarbonyl, C2-8 heterocycloalkenyl alkyl containing nitrogen as a heteroatom, Formula 2

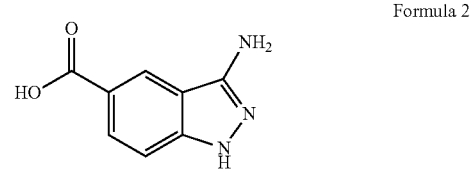

Formula 3

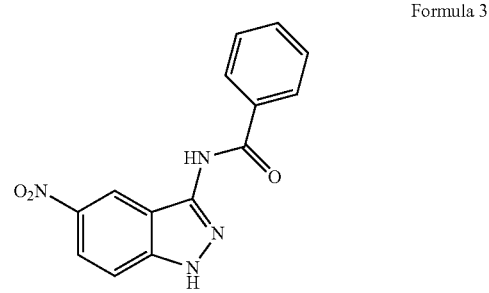

Formula 4

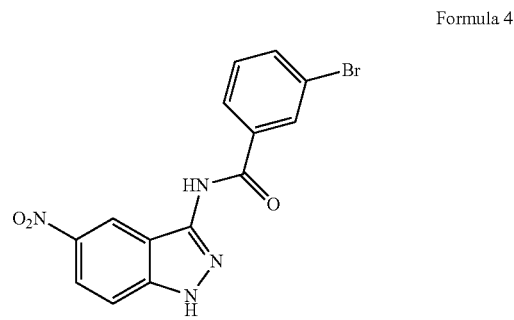

-continued
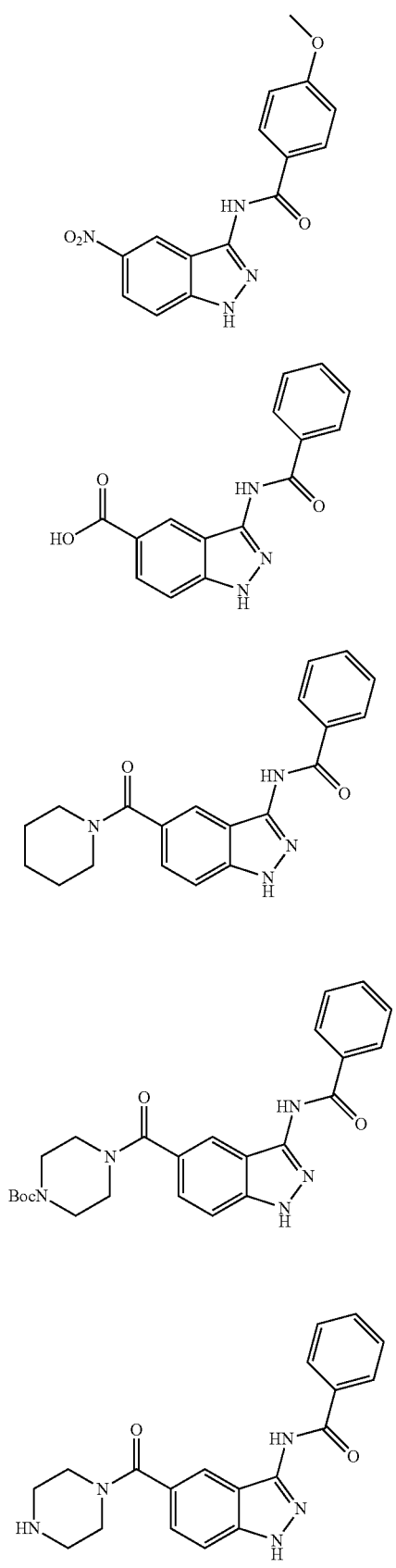
Formula 5
Formula 6
Formula 7
Formula 8
Formula 9
-continued
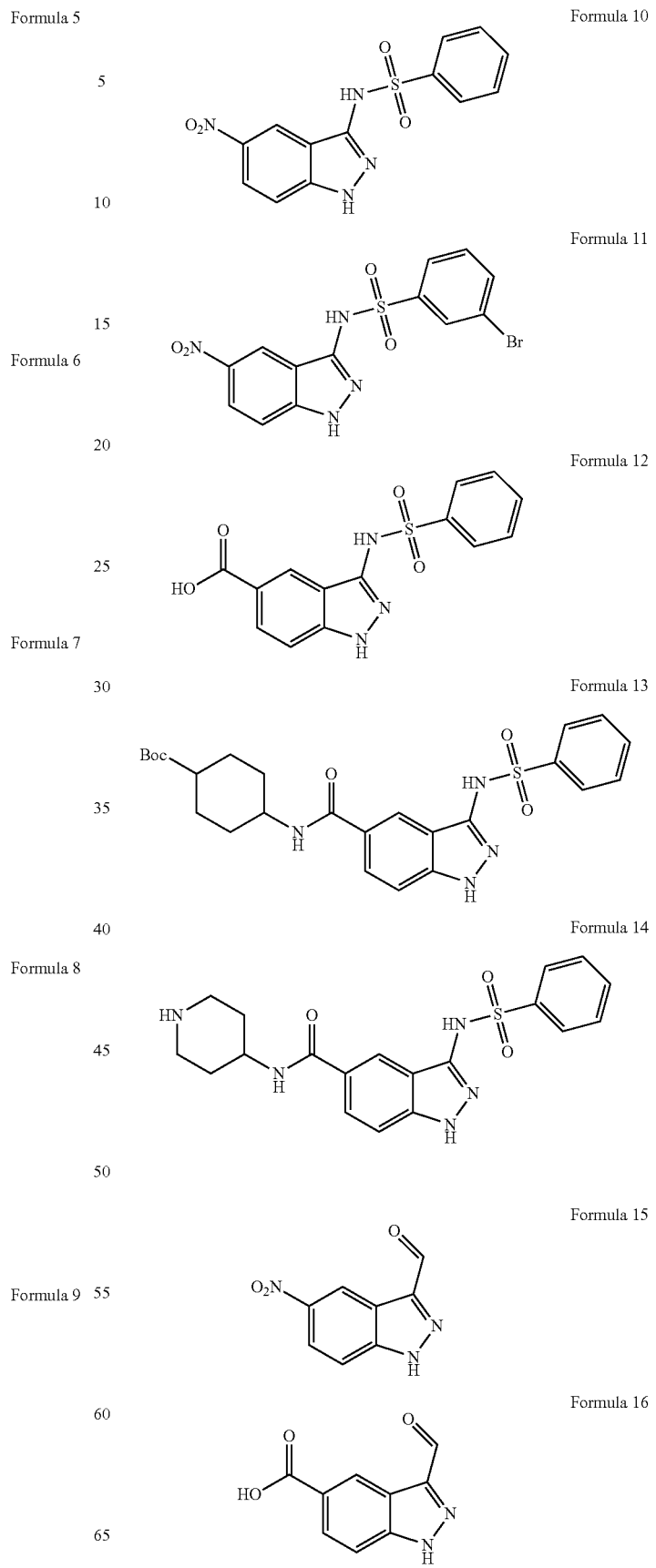
Formula 10
Formula 11
Formula 12
Formula 13
Formula 14
Formula 15
Formula 16

-continued
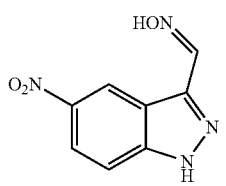
Formula 17
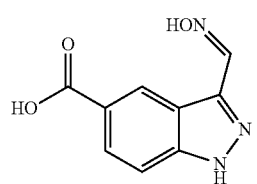
Formula 18
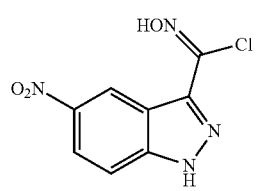
Formula 19
Formula 20
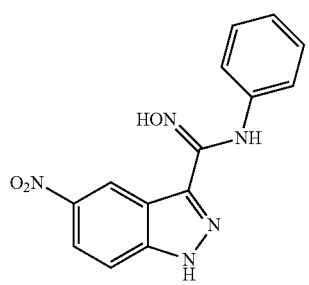
Formula 21
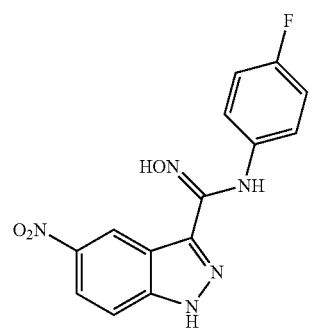
Formula 22
-continued
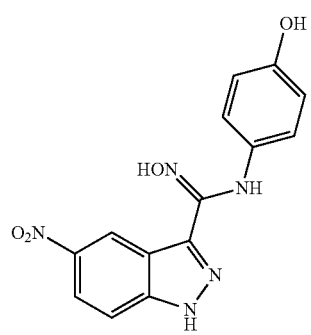
Formula 23
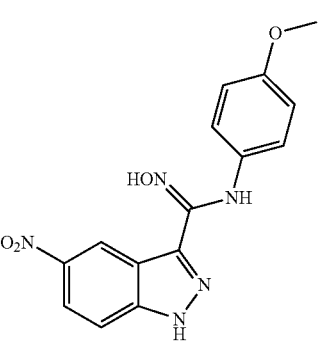
Formula 24
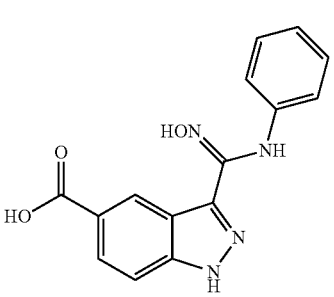
Formula 25
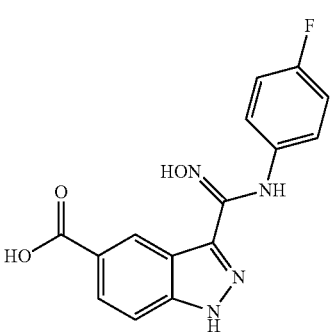
Formula 26
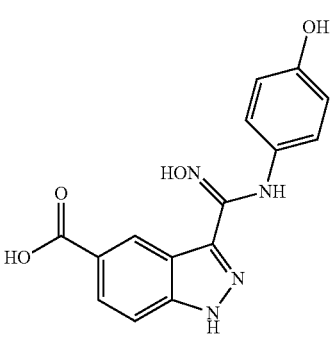
Formula 27

Formula 28
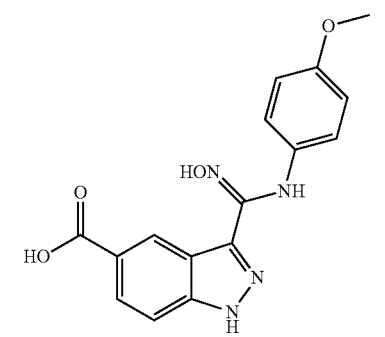
Formula 29
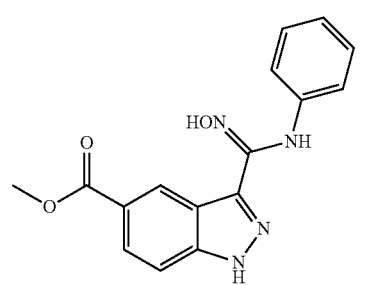
Formula 30
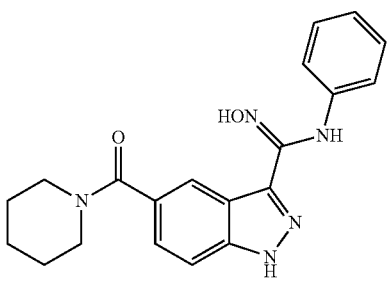
Formula 31
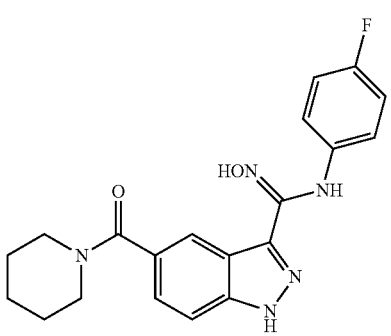
Formula 32
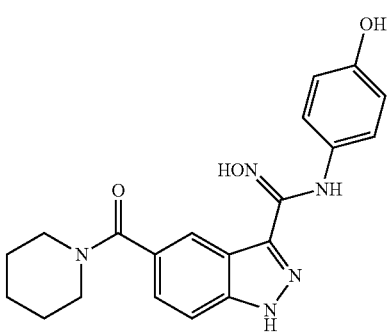
Formula 33
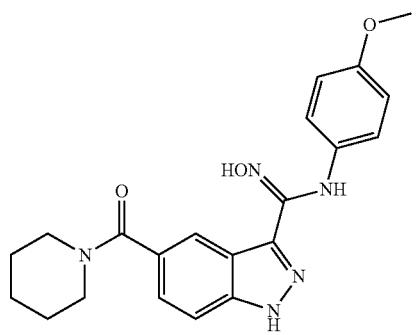
Formula 34
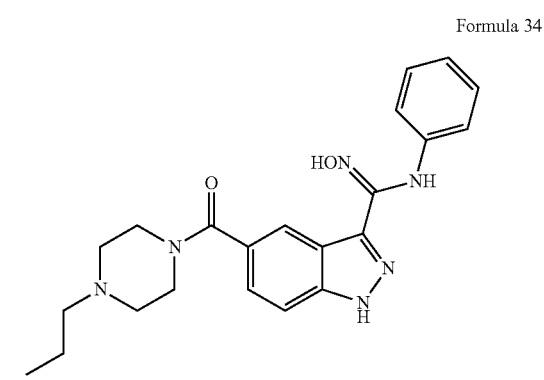
Formula 35
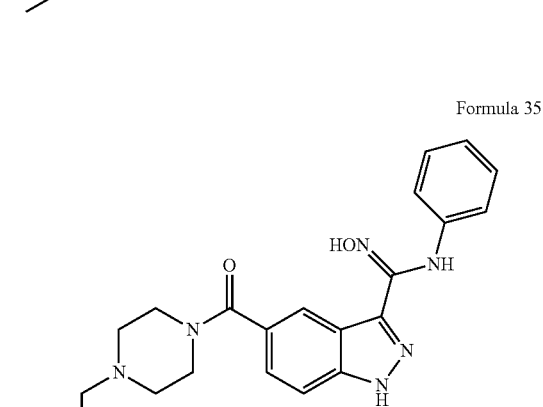
Formula 36
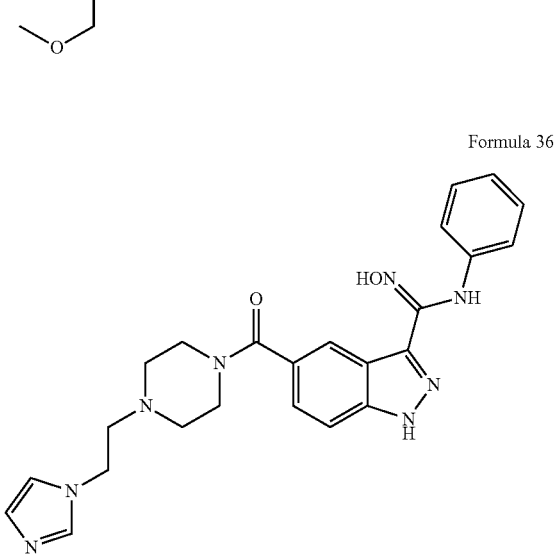

Formula 37
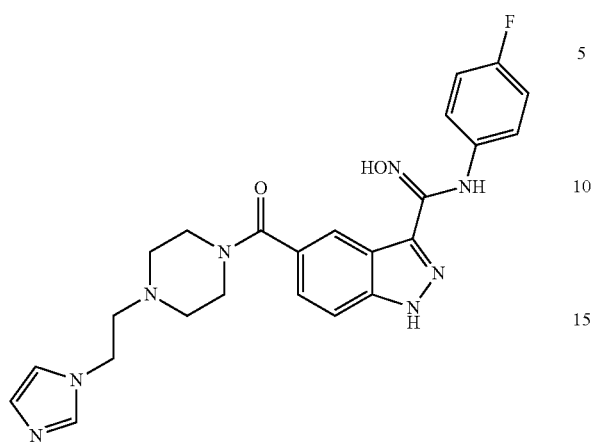
Formula 38
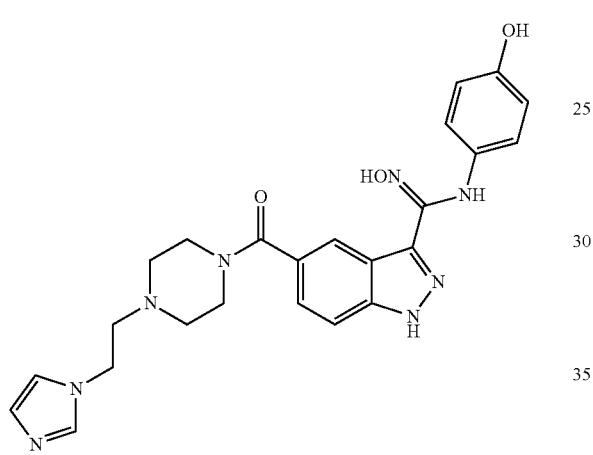
Formula 39
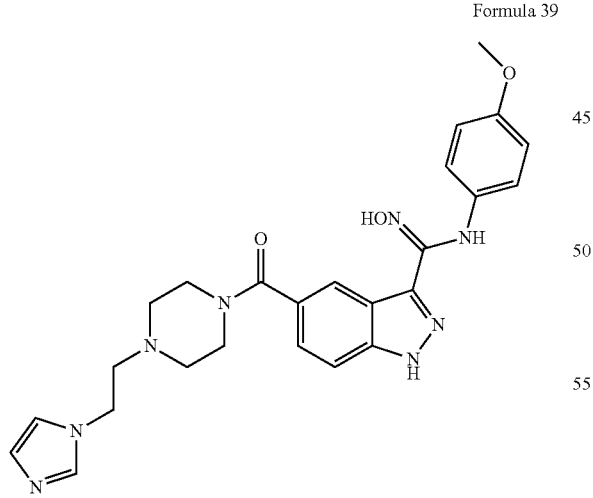
Formula 40
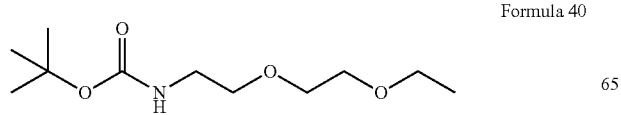
Formula 41
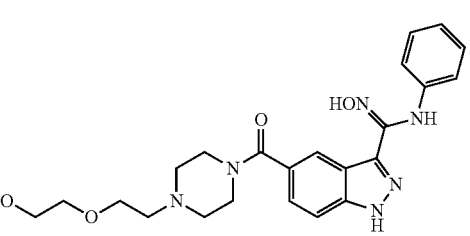
Formula 42
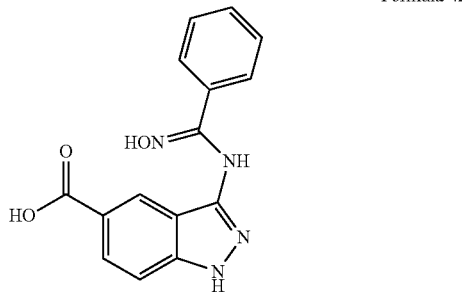
Formula 43
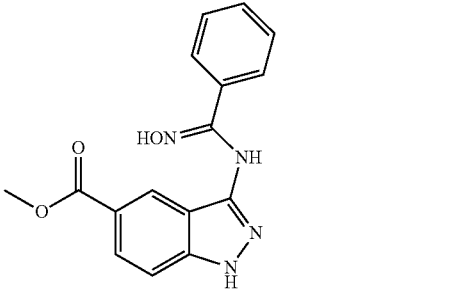
Formula 44
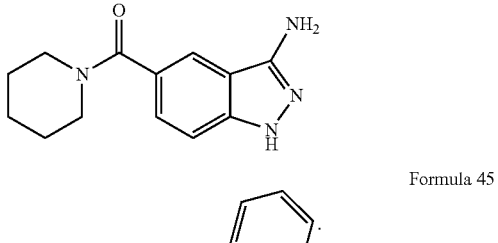
Formula 45
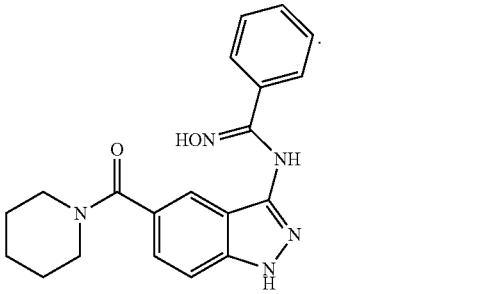

16. The method of claim 10, wherein the compound is represented by a formula selected from the group consisting of the following formulas 1, 25, 30, 31, 33, 34, 35 and 45:
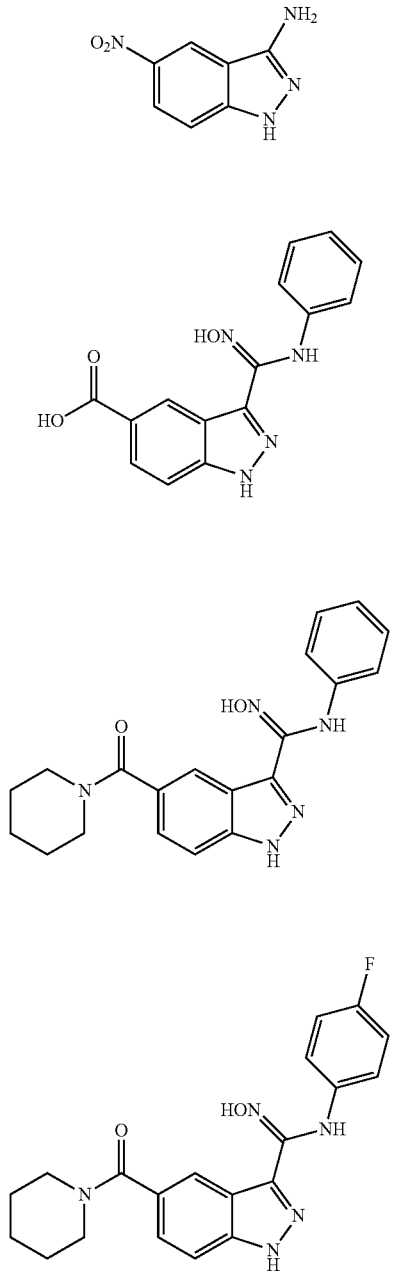
Formula 1
Formula 25
Formula 30
Formula 31
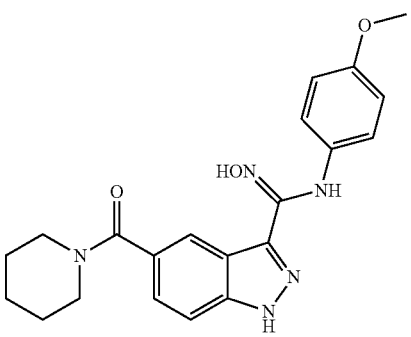
Formula 33
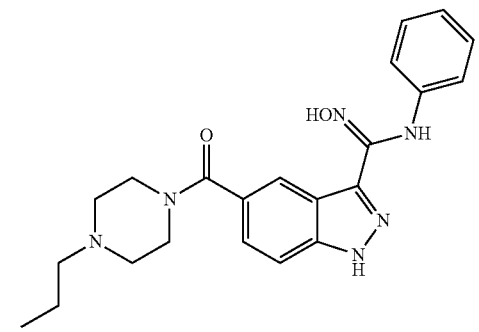
Formula 34
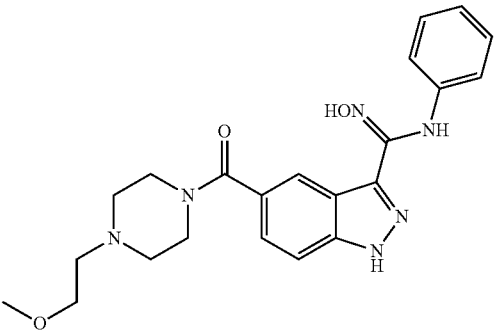
Formula 35
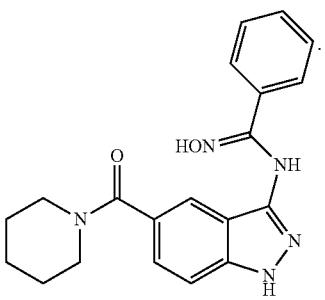
Formula 45
* * * * *